US011399985B2

(12) United States Patent
Yamamoto et al.

(10) Patent No.: US 11,399,985 B2
(45) Date of Patent: Aug. 2, 2022

(54) ABSORBENT ARTICLE FOR ANIMALS

(71) Applicant: Unicharm Corporation, Ehime (JP)

(72) Inventors: Hiroki Yamamoto, Kanonji (JP); Daisuke Komatsubara, Kanonji (JP)

(73) Assignee: Unicharm Corporation, Ehime (JP)

( * ) Notice: Subject to any disclaimer, the term of this patent is extended or adjusted under 35 U.S.C. 154(b) by 376 days.

(21) Appl. No.: 16/457,146

(22) Filed: Jun. 28, 2019

(65) Prior Publication Data
US 2020/0000061 A1    Jan. 2, 2020

(30) Foreign Application Priority Data

Jun. 29, 2018  (JP) .............................. JP2018-124833
Jun. 29, 2018  (JP) .............................. JP2018-124998

(51) Int. Cl.
A61F 13/15     (2006.01)
B32B 5/02      (2006.01)
B32B 5/26      (2006.01)
B32B 27/12     (2006.01)
B32B 7/12      (2006.01)
A01K 23/00     (2006.01)

(52) U.S. Cl.
CPC .............. A61F 13/15 (2013.01); B32B 5/022 (2013.01); B32B 5/26 (2013.01); B32B 7/12 (2013.01); B32B 27/12 (2013.01); A01K 23/00 (2013.01); B32B 2262/02 (2013.01); B32B 2307/7265 (2013.01); B32B 2555/02 (2013.01)

(58) Field of Classification Search
CPC ........... A61F 13/15; B32B 5/022; B32B 5/26; B32B 7/112; B32B 27/12; B32B 2262/02; B32B 2307/7265; B32B 2555/02; A01K 23/00
See application file for complete search history.

(56) References Cited

U.S. PATENT DOCUMENTS

2014/0083372 A1    3/2014  Komatsubara et al.
2015/0045762 A1*   2/2015  Komatsubara ......... A01K 23/00
                                              604/385.201

FOREIGN PATENT DOCUMENTS

JP    2012-205578 A    10/2012
JP    2012205575 A     10/2012
JP    2014198195 A     10/2014

* cited by examiner

Primary Examiner — Jacqueline F Stephens
(74) Attorney, Agent, or Firm — Osha Bergman Watanabe & Burton LLP

(57) ABSTRACT

An absorbent article for animals that includes a longitudinal direction, a width direction, and a thickness direction that are mutually orthogonal to each other. The absorbent article includes: a first nonwoven fabric that forms a first surface in the thickness direction; a second nonwoven fabric that forms a second surface in the thickness direction that is on an opposite side of the first surface, and that is attached to an animal such that the longitudinal direction is disposed along a waist of the animal; in a plan view, between a first side edge and a second side edge of the absorbent article in the longitudinal direction, a first region, a center region, and a second region that divide the absorbent article into three equal portions in the longitudinal direction; and an engagement portion that extends in the width direction in the first surface of the first region.

10 Claims, 24 Drawing Sheets

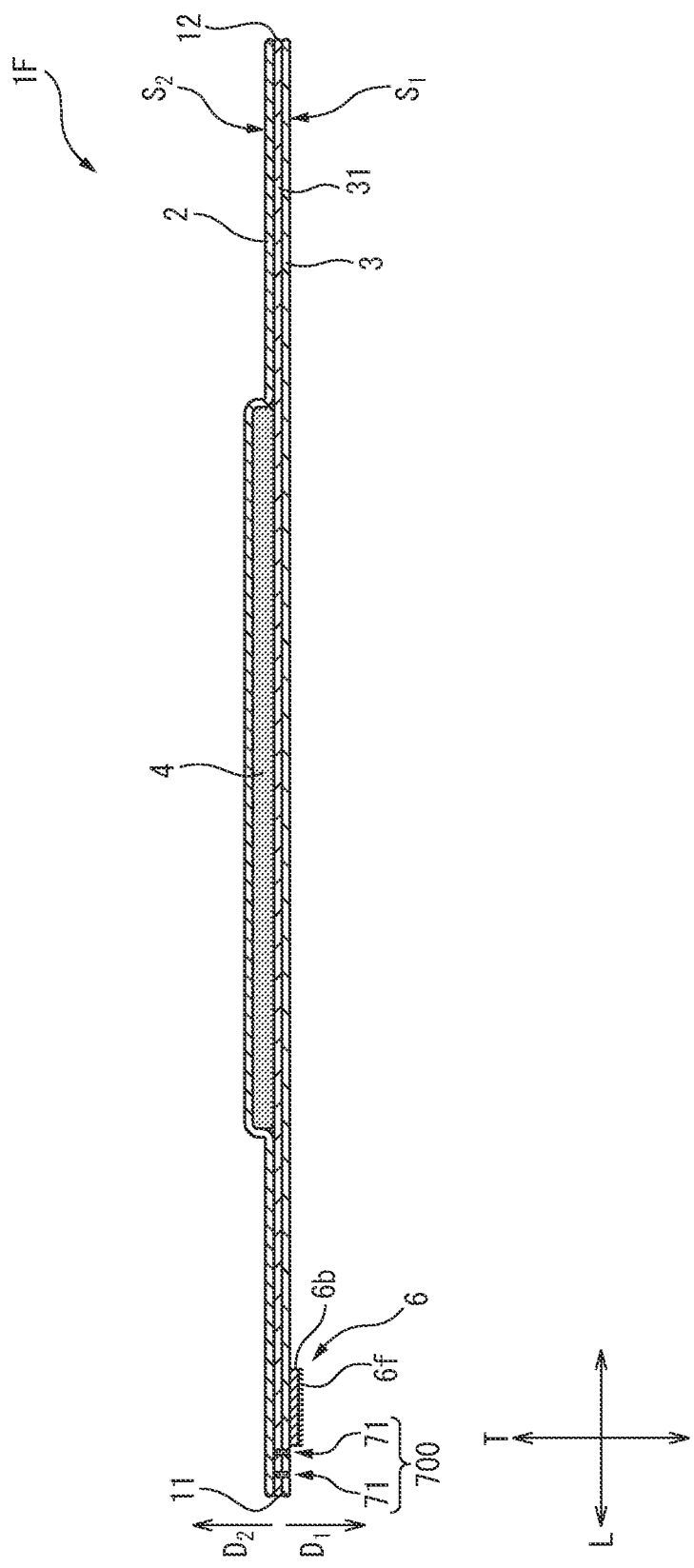
F I G. 16

ABSORBENT ARTICLE FOR ANIMALS

TECHNICAL FIELD

The present disclosure generally relates to an absorbent article for animals, such as a disposable diaper, etc., to be used for animals such as a dog, a cat, etc.

BACKGROUND

As an absorbent article for animals so as to handle excrements such as urine, etc., excreted by animals such as a dog, a cat, etc., a belt-like absorbent article for animals which is wound around and attached to the waist of an animal is known.

As such a belt-like absorbent article for animals, for example, in Patent Literature 1, disclosed is an absorbent article for pets which is disposed so that the front surface layer side of the first end portion in the longitudinal direction faces the body side of a pet, and the front surface layer side of the second end portion in the longitudinal direction is detachably attached to the back surface layer side of the first end portion, in a state of being wound around the waist of the pet, comprising a locking member which is disposed on the back surface layer side of the first end portion, is configured in a rectangular shape, and the longitudinal direction thereof extends along the width direction of the absorbent article for pets, and a pair of bending line portions which are formed in the first end portion, and function as starting points for a pair of side portion sides in the first 1 end portion to bend toward the front surface layer side.

Patent Literature 1: Japanese Unexamined Patent Publication No. 2012-205578

However, as in the absorbent article for pets disclosed in Patent Literature 1, when the back surface layer of the absorbent article for animals comprising an engagement portion (an engagement member) on the back surface layer in one side end portion region in the longitudinal direction (refer to FIG. 23) is formed by a material which is soft and can easily be engaged, such as a nonwoven fabric, there have been cases in which during the manufacture and conveyance processes of the absorbent article, or at the time of putting on the absorbent article, etc., the flap portion which is positioned between the one side edge in the longitudinal direction of the absorbent article and the engagement portion is bent toward the back surface layer side as shown in FIG. 24(a), and the surface on the back surface layer side of the flap portion (that is, the surface of the nonwoven fabric which forms the back surface layer) engages with the above mentioned engagement portion so as to be adhered to the engagement portion.

When the flap portion is adhered to the engagement portion in this manner, it is necessary to tear off the flap portion adhered to the engagement portion from the engagement portion at the time of attaching the absorbent article to the torso of an animal, however, in a case in which the flap portion is adhered to the engagement portion up to the one side edge in the longitudinal direction of the absorbent article, it is difficult to tear off the flap portion from the engagement portion, and there may have been cases in which it took a lot of trouble when attaching the absorbent article to the torso of an animal.

Further, as in the absorbent article for pets disclosed in Patent Literature 1, when the back surface layer of the absorbent article for animals comprising an engagement portion (an engagement member) on the back surface layer in one side end portion region in the longitudinal direction (refer to FIG. 23) is formed by a material which is soft and can easily be engaged, such as a nonwoven fabric, there have been cases in which during the manufacture and conveyance processes of the absorbent article, or at the time of putting on the absorbent article, etc., a portion of the one side end portion in the longitudinal direction (to be more specific, the flap portion which is positioned between the one side edge in the longitudinal direction of the absorbent article and the engagement portion, and the portion on the inner side in the longitudinal direction with respect to the engagement portion (hereinbelow, these portions may be collectively referred to simply as "the flap portion, etc.")) is bent toward the back surface layer side as shown in FIG. 24(b) and FIG. 24(c), and the surface on the back surface layer side of such region (that is, the surface of the nonwoven fabric which forms the back surface layer) engages with the above mentioned engagement portion so as to be adhered to the engagement portion.

When the flap portion, etc., is adhered to the engagement portion in this manner, it is necessary to tear off the flap portion, etc., adhered to the engagement portion from the engagement portion at the time of attaching the absorbent article to the torso of an animal, however, since the configurational fibers of the nonwoven fabric which forms the back surface layer remain in the engagement portion after tearing off the flap portion, etc., there may have been cases in which the engagement force (the joining strength) of the engagement portion is decreased so that the absorbent article which is attached to the torso of an animal can easily come off.

SUMMARY

One or more embodiments provide an absorbent article for animals that is capable of easily tearing off the flap portion from the engagement portion even when having been adhered thereto, and it does not take much trouble to be attached to the torso of an animal.

One or more embodiments provide an absorbent article for animals in which it is difficult for the engagement force of the engagement portion to be decreased and which is difficult to come off from the torso of the attached animal.

In one or more embodiments, an absorbent article for animals which includes a longitudinal direction, a width direction, and a thickness direction that are mutually orthogonal to each other, further includes in the thickness direction a first surface and a second surface that is on an opposite side of the first surface, and which is attached to an animal so that the longitudinal direction is located along a waist of the animal, the absorbent article further including in the thickness direction a nonwoven fabric which forms the first surface and a nonwoven fabric which forms the second surface, and in a plan view, between one side edge and the other side edge in the longitudinal direction, a first region, a center region, and a second region which divide the absorbent article into three equal portions in the longitudinal direction, wherein the absorbent article comprises:
  an engagement portion which extends in the width direction in the first surface of the first region and engages in a detachable manner with the second surface of the second region, and
  in the longitudinal direction, a flap portion which extends from one side edge in the longitudinal direction of the engagement portion to the one side edge in the longitudinal direction of the absorbent article, wherein the flap portion has a longitudinal direction length which is longer than a longitudinal direction length of the engagement portion.

Since in the absorbent article for animals according to one or more embodiments, the flap portion has a longitudinal direction length which is longer than a longitudinal direction length of the engagement portion, even when the flap portion is bent toward the first surface side as described above so as to be adhered to the engagement portion, by grasping the portion which is longer than the longitudinal direction length of the engagement portion in the flap portion (hereinbelow, such portion may be referred to as "the surplus portion") as the grasping portion, the flap portion can be easily torn off from the engagement portion.

Accordingly, the absorbent article for animals according to one or more embodiments can make it possible so that it does not take much trouble to be attached to the torso of an animal.

In the absorbent article for animals according to one or more embodiments, the engagement portion includes, at a portion in the width direction, an engagement element non-disposed portion in which an engagement element is not disposed.

Since the absorbent article for animals according to one or more embodiments includes at a portion in the width direction the engagement element non-disposed portion in which an engagement element is not disposed, when the flap portion is bent toward the first surface side so as to be adhered to the engagement portion, the above described engagement element non-disposed portion can also function as the grasping portion, whereby a wider area of the grasping portion can be secured.

Accordingly, the absorbent article according to one or more embodiments can even more easily tear off the flap portion which has been adhered to the engagement portion.

In the absorbent article for animals according to one or more embodiments, the engagement portion includes, at a portion in the width direction, an engagement element crushed portion which is formed by crushing an engagement element.

Since the absorbent article for animals according to one or more embodiments includes at a portion in the width direction an engagement element crushed portion which is formed by crushing an engagement element, when the flap portion is bent toward the first surface side so as to be adhered to the engagement portion, the above described engagement element crushed portion can also function as the grasping portion, whereby a wider area of the grasping portion can be secured.

Accordingly, the absorbent article according to one or more embodiments can even more easily tear off the flap portion which has been adhered to the engagement portion.

In the absorbent article for animals according to one or more embodiments, the engagement element crushed portion is disposed at a position which includes at least one edge of one side edge and the other side edge in the width direction of the engagement portion.

Since in the absorbent article for animals according to one or more embodiments, the engagement element crushed portion which can function as the above described grasping portion is disposed at a position which includes at least one edge of one side edge and the other side edge in the width direction of the engagement portion, when tearing off the flap portion from the engagement portion by grasping the engagement element crushed portion as well as the above described surplus portion as the grasping portion, the flap portion can be torn off sequentially from the one side edge or the other side edge in the width direction of the engagement portion, whereby the flap portion can be torn off from the engagement portion with less force compared to the case of tearing the flap portion from the one side edge in the longitudinal direction.

The absorbent article for animals according to one or more embodiments, further includes
in a plan view, two bending lines which extend in the longitudinal direction at positions which pass one side edge and the other side edge in the width direction of the engagement portion, or at positions on an outer side in the width direction with respect to the one side edge and the other side edge, wherein
each of one side end portion and the other side end portion in the width direction of the absorbent article is folded toward a second surface side at each of the bending lines.

Since in the absorbent article for animals according to one or more embodiments, each of one side end portion and the other side end portion in the width direction is folded toward a second surface side at the bending lines which are positioned at the above described specific positions, in addition to being able to make it difficult for the flap portion to be bent toward the first surface side, even when the flap portion is bent toward the first surface side so as to be adhered to the engagement portion, the flap portion can be easily torn off from the engagement portion only by spreading the one side end portion and the other side end portion in the width direction of the above described absorbent article which is folded toward the second surface side, or by pulling the one side end portion and the other side end portion toward the outer side in the width direction.

Accordingly, since the absorbent article according to one or more embodiments can secure the tearing means of the flap portion other than the surplus portion which functions as the above described grasping portion, the flap portion can be easily torn off from the engagement portion in a more reliable manner.

The absorbent article for animals according to one or more embodiments, further included
in a plan view, an elastic member which extends in the longitudinal direction at each of one side end portion and the other side end portion in the width direction, wherein
each of the elastic members is disposed, in a plan view, so as to overlap with the flap portion.

Since in the absorbent article for animals according to one or more embodiments, at each of one side end portion and the other side end portion in the width direction, an elastic member which extends in the longitudinal direction is disposed so as to overlap with the flap portion in a plan view, even when the flap portion is bent toward the first surface side so as to be adhered to the engagement portion, the flap portion can be torn off from the engagement portion with less force by the stretching and shrinking action of the elastic member in the flap portion.

The absorbent article for animals according to one or more embodiments, further includes
an absorbent body which is disposed between the nonwoven fabric that forms the first surface and the nonwoven fabric that forms the second surface in the thickness direction, and extends across from the first region to the second region in a plan view, wherein
one side edge in the longitudinal direction of the absorbent body overlaps with the engagement portion in the thickness direction.

Since in the absorbent article for animals according to one or more embodiments, one side edge in the longitudinal direction of the absorbent body overlaps with the engagement portion in the thickness direction, and the portion with high rigidity can be continuously secured from the engagement portion toward the inner side in the longitudinal direction by the existence of the absorbent body, even when the flap portion which has a relatively lower rigidity is bent toward the first surface side so as to be adhered to the engagement portion, the flap portion can be more easily torn off from the engagement portion.

In an absorbent article for animals which includes a longitudinal direction, a width direction, and a thickness direction that are mutually orthogonal to each other, further includes in the thickness direction a first surface and a second surface that is on an opposite side of the first surface, and which is attached to an animal so that the longitudinal direction is located along a waist of the animal, the absorbent article according to one or more embodiments further including in the thickness direction a nonwoven fabric which forms the first surface and a nonwoven fabric which forms the second surface, and in a plan view, between one side edge and the other side edge in the longitudinal direction, a first region, a center region, and a second region which divide the absorbent article into three equal portions in the longitudinal direction, wherein the absorbent article comprises:

an engagement portion which extends in the width direction in the first surface of the first region and engages in a detachable manner with the second surface of the second region, and a compressed portion formation region which, in a plan view, at least partially overlaps with an engagement portion peripheral region in which a longitudinal direction distance from the engagement portion is or less than a longitudinal direction length of the engagement portion, and includes one or a plurality of compressed portions which are depressed from the first surface in the thickness direction, wherein the first region has a compressed portion area ratio which is greater than a compressed portion area ratio in the second region.

The absorbent article for animals according to one or more embodiments includes one or a plurality of compressed portions in the engagement portion peripheral region of the above described first region, and since it is difficult for the engagement portion peripheral region to be bent by the compressed portion with high rigidity, it is difficult for the above described flap portion, etc., to be adhered to the engagement portion, and as a result, it is difficult for the engagement force of the engagement portion to be decreased.

Further, even if the engagement portion peripheral region is bent toward the first surface side and the flap portion, etc., is adhered to the engagement portion, since the surface of the first surface side of the compressed portion is formed to be a surface with high fiber density and smoothness due to the configurational fibers of the nonwoven fabric which forms the first surface being compacted, it is easy for the flap portion, etc., which has been adhered to the engagement portion to be torn off from the engagement portion, and further, also when the flap portion, etc. is torn off from the engagement portion, it is difficult for the configurational fibers of the nonwoven fabric which forms the adhered surface (the first surface) of the flap portion, etc. to come off (that is, it is difficult for the configurational fibers of the nonwoven fabric which forms the first surface of the flap portion, etc. to remain in the engagement portion after tearing off the flap portion, etc.), and as a result, it is difficult for the engagement force of the engagement portion to be decreased.

Still further, in the absorbent article for animals according to one or more embodiments, the compressed portion area ratio in the first region is configured to be greater than the compressed portion area ratio in the second region, and since the second region has a relatively lower rigidity and is soft, the second region can engage with the engagement portion in the above described first region with high joining strength while following the shape of the torso of an animal.

As described above, in the absorbent article for animals according to one or more embodiments, it is difficult for the engagement force of the engagement portion to be decreased and it is difficult to come off from the torso of the attached animal.

In the absorbent article for animals according to one or more embodiments, the compressed portion formation region having a width direction length which is longer than a width direction length of the engagement portion.

Since in the absorbent article for animals according to one or more embodiments, the compressed portion formation region has a width direction length which is longer than a width direction length of the engagement portion, not only the absorbent article can make it difficult for the wider range of region in the width direction of the flap portion, etc. to be bent, but also even if the flap portion, etc. is bent (especially, even in a case in which the end portion in the width direction of the absorbent article is also bent), the possibility of the flap portion, etc. being adhered to the engagement portion can be more decreased.

As described above, by the absorbent article for animals according to one or more embodiments, it is more difficult for the engagement force of the engagement portion to be decreased and it is more difficult to come off from the torso of the attached animal.

In the absorbent article for animals according to one or more embodiments, the compressed portion formation region extending in the longitudinal direction, from one side edge in the longitudinal direction of the engagement portion to the one side edge in the longitudinal direction of the absorbent article.

Since in the absorbent article for animals according to one or more embodiments, the compressed portion formation region extends in the longitudinal direction, from one side edge in the longitudinal direction of the engagement portion to the one side edge in the longitudinal direction of the absorbent article, that is, the compressed portion formation region extends across the entire flap portion, the absorbent article can make it difficult for especially the flap portion to be bent, and even if the flap portion is bent, the possibility of the bent flap portion being adhered to the engagement portion can be more reliably decreased, regardless of how the flap portion is bent.

In the absorbent article for animals according to one or more embodiments, the compressed portion formation region extending in the longitudinal direction from one side edge in the longitudinal direction of the engagement portion toward an outer side in the longitudinal direction, and has a longitudinal direction length which is longer than the longitudinal direction length of the engagement portion.

Since in the absorbent article for animals according to one or more embodiments, the compressed portion formation region extends in the longitudinal direction from one side edge in the longitudinal direction of the engagement portion toward an outer side in the longitudinal direction, and has a longitudinal direction length which is longer than a longitudinal direction length of the engagement portion, especially even in a case in which the flap portion is formed to be long in the longitudinal direction, not only the absorbent article can make it difficult for the portion which affects the adhesion of the flap portion to the engagement portion to be bent, but also even if the flap portion is bent, the possibility of the bent flap portion being adhered to the engagement portion can be more reliably decreased.

Further, since in the absorbent article for animals according to one or more embodiments, the compressed portion formation region extends in the longitudinal direction from one side edge in the longitudinal direction of the engagement portion toward an outer side in the longitudinal direction, and has a longitudinal direction length which is longer than a longitudinal direction length of the engagement portion, that is, since the flap portion has a longitudinal direction length which is longer than a longitudinal direction length of the engagement portion, when the flap portion is adhered to the engagement portion, by regarding the portion longer than the longitudinal direction length of the engagement portion in the flap portion as the grasping portion, the flap portion can be easily torn off by grasping the grasping portion, and the advantage of not taking much trouble in attaching the absorbent article for animals to the torso of an animal can also be obtained.

In the absorbent article for animals according to one or more embodiments, the compressed portion formation region extending in the longitudinal direction from the other side edge in the longitudinal direction of the engagement portion toward an inner side in the longitudinal direction, and has a longitudinal direction length which is longer than the longitudinal direction length of the engagement portion.

Since in the absorbent article for animals according to one or more embodiments, the compressed portion formation region extends in the longitudinal direction from the other side edge in the longitudinal direction of the engagement portion toward an inner side in the longitudinal direction, and has a longitudinal direction length which is longer than a longitudinal direction length of the engagement portion, not only the absorbent article can make it difficult for the portion which affects the adhesion to the engagement portion, especially in the portion on the inner side in the longitudinal direction with respect to the engagement portion, to be bent, but also even if the portion on the inner side in the longitudinal direction with respect to the engagement portion is bent, the possibility of the bent portion being adhered to the engagement portion can be more reliably decreased.

The absorbent article for animals according to one or more embodiments, further includes
  a liquid impermeable member which is disposed between the nonwoven fabric that forms the first surface and the nonwoven fabric that forms the second surface, and
  a joining portion which joins at least a surface on a first surface side of the liquid impermeable member and a surface on a second surface side of the nonwoven fabric which forms the first surface, wherein
  the joining portion includes, in the compressed portion formation region, a non-overlapping portion which does not overlap with the compressed portion in a plan view.

Since in the absorbent article for animals according to one or more embodiments, the joining portion which joins a surface on a first surface side of the liquid impermeable member and a surface on a second surface side of the nonwoven fabric which forms the first surface includes in the above described compressed portion formation region, a non-overlapping portion which does not overlap with the compressed portion in a plan view, the absorbent article can make it difficult for the nonwoven fabric which forms the first surface to be lifted up between the adjacent compressed portions in the compressed portion formation region. Accordingly, even when the above described flap portion, etc. is bent and the compressed portion formation region comes close to the engagement portion, since it is difficult not only for the above described compressed portion but also for the non-overlapping portion to be in contact with the above described engagement portion, the possibility of the compressed portion formation region being adhered to the engagement portion can be more reliably decreased.

The absorbent article for animals according to one or more embodiments, further includes
  a first bending line which extends in the width direction and overlaps in a plan view with a longitudinal direction central axis line that extends in the width direction, for folding the absorbent article so that the second surface is to be located on an inner side,
  two second bending lines which extend in the width direction and which are positioned, in a plan view, between the one side edge in the longitudinal direction of the absorbent article and the first bending line, and between the other side edge in the longitudinal direction of the absorbent article and the first bending line, for further folding the absorbent article which has been folded at the first bending line so that the engagement portion is to be located on the inner side, and
  an inner side compressed portion formation region which includes the one or the plurality of compressed portions that are depressed from the first surface in the thickness direction, in the first surface of a region that is in a symmetrical relationship with the engagement portion, with the second bending line that is positioned between the one side edge in the longitudinal direction of the absorbent article and the first bending line as a target axis.

Since the absorbent article for animals according to one or more embodiments further includes an inner side compressed portion formation region which includes one or a plurality of compressed portions that are depressed from the first surface in the thickness direction, in the first surface of a region that is in a symmetrical relationship with the engagement portion, with the above described second bending line as a target axis, even when a plurality of absorbent articles are folded at the first bending line and the second bending line so as to be packaged, it is difficult for the above described engagement portion to be engaged with the inner side compressed portion formation region in the folded absorbent articles, and it is difficult for the engagement force of the engagement portion to be decreased.

According to one or more embodiments of the present invention, an absorbent article for animals which is capable of easily tearing off the flap portion from the engagement portion even when having been adhered thereto, and it does not take much trouble to be attached to the torso of an animal can be provided. Further, according to one or more embodiments of the present invention, an absorbent article for animals in which it is difficult for the engagement force of the engagement portion to be decreased and which is difficult to come off from the torso of the attached animal can also be provided.

BRIEF DESCRIPTION OF DRAWINGS

FIG. 16 is an end view of the longitudinal direction cross section along the width direction central axis line $C_L$ which extends in the longitudinal direction L of the diaper for pets 1F according to one or more embodiments.

DETAILED DESCRIPTION

Figure 1:
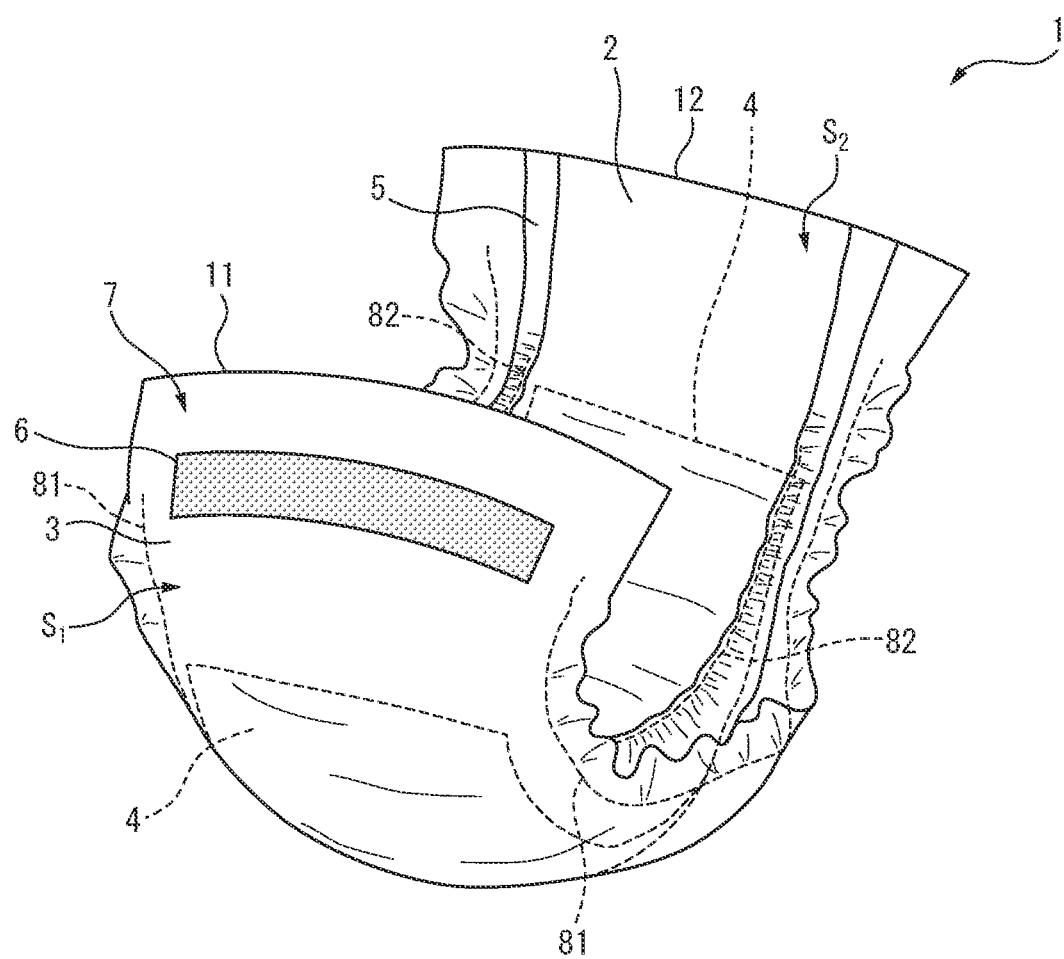
FIG. 1 is a perspective view of the diaper for pets 1 according to one or more embodiments.

Hereinbelow, embodiments of the absorbent article for animals according to the present invention are explained in detail with reference to the drawings. Incidentally, in the present description, unless otherwise noted, "viewing an object (for example, the absorbent article for animals, the absorbent body, etc.) which is placed on a horizontal plane in an expanded state from the upper side in the vertical direction in the thickness direction of the object" is referred to as "a plan view." Especially, in a case in which the object is the absorbent article for animals, viewing the absorbent article in an expanded state from the first surface side in the thickness direction may be referred to simply as "a plan view."

Various directions, etc., which are used in the present description are as follows, unless otherwise noted.

In the present description, "the longitudinal direction" refers to "the direction in which the length of the absorbent article for animals in a plan view is longer", "the width direction" refers to "the direction in which the length of the absorbent article for animals in a plan view is shorter (short direction)", and "the thickness direction" refers to "the vertical direction with respect to the absorbent article for animals which is placed on a horizontal plane in an expanded state". These longitudinal direction, the width direction and the thickness direction are in a relationship of being mutually orthogonal to each other.

Further, in the present description, unless otherwise noted, "the relatively closer side with respect to the longitudinal direction central axis line $C_W$ which extends in the width direction, in the longitudinal direction of the absorbent article for animals" is referred to as "the inner side in the longitudinal direction", and "the relatively farther side with respect to the longitudinal direction central axis line $C_W$ which extends in the width direction, in the longitudinal direction of the absorbent article for animals" is referred to as "the outer side in the longitudinal direction". In the same manner, "the relatively closer side with respect to the width direction central axis line $C_L$ which extends in the longitudinal direction, in the width direction of the absorbent article for animals" is referred to as "the inner side in the width direction", and "the relatively farther side with respect to the width direction central axis line $C_L$ which extends in the longitudinal direction, in the width direction of the absorbent article for animals" is referred to as "the outer side in the width direction".

Still further, in the present description, unless otherwise noted, "in the thickness direction of the absorbent article for animals, the relatively closer side with respect to the torso of an animal, when the absorbent article is attached to the torso of the animal" is referred to as "the torso facing surface side", and "in the thickness direction of the absorbent article for animals, the relatively farther side with respect to the torso of an animal, when the absorbent article is attached to the torso of the animal" is referred to as "the torso non-facing surface side". Incidentally, in the present description, "the surface on the torso facing surface side" and "the surface on the torso non-facing surface side" of the absorbent article for animals and the configurational members (for example, the top sheet, the absorbent body, the back film, the back sheet, etc.) may be referred to simply as "the torso facing surface" and "the torso non-facing surface," respectively.

Hereinbelow, embodiments of the present invention are explained in detail with reference to the drawings.

Figure 2:
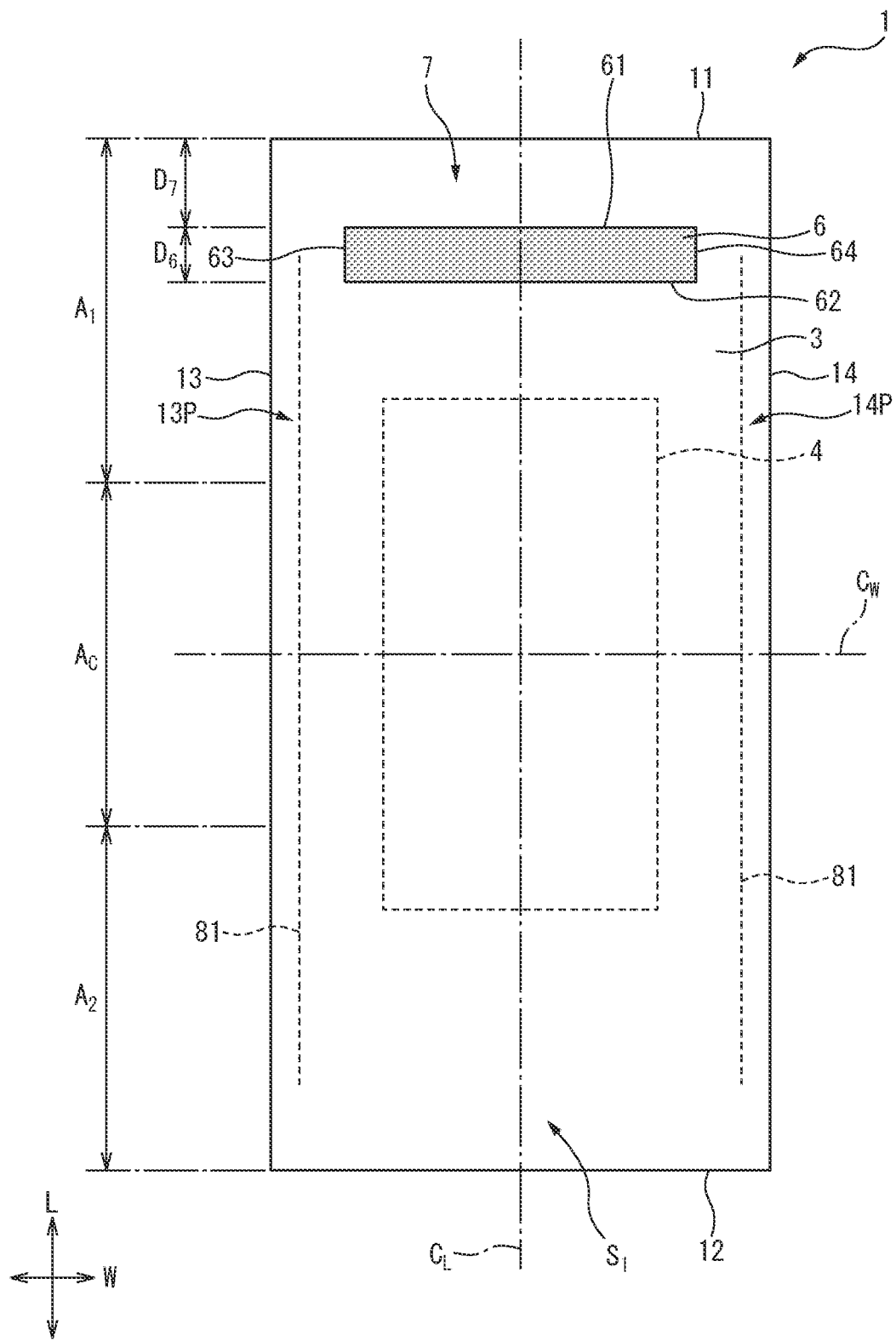
FIG. 2 is a plan view of the diaper for pets 1 in an expanded state viewed from the first surface side (the back sheet side) in the thickness direction T according to one or more embodiments.
Figure 3:
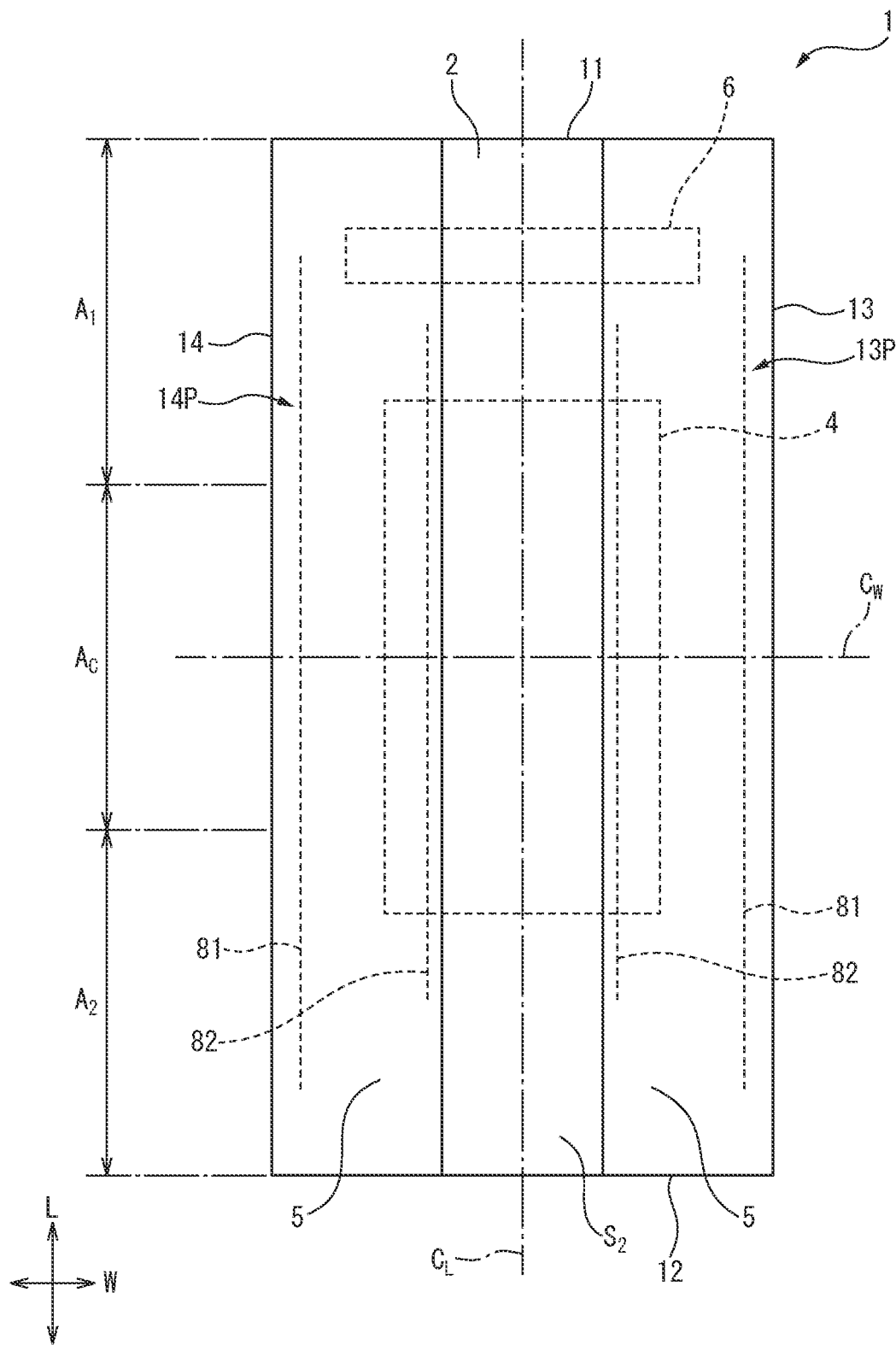
FIG. 3 is a plan view of the diaper for pets 1 in an expanded state viewed from the second surface side (the top sheet side) in the thickness direction T according to one or more embodiments.
Figure 4:
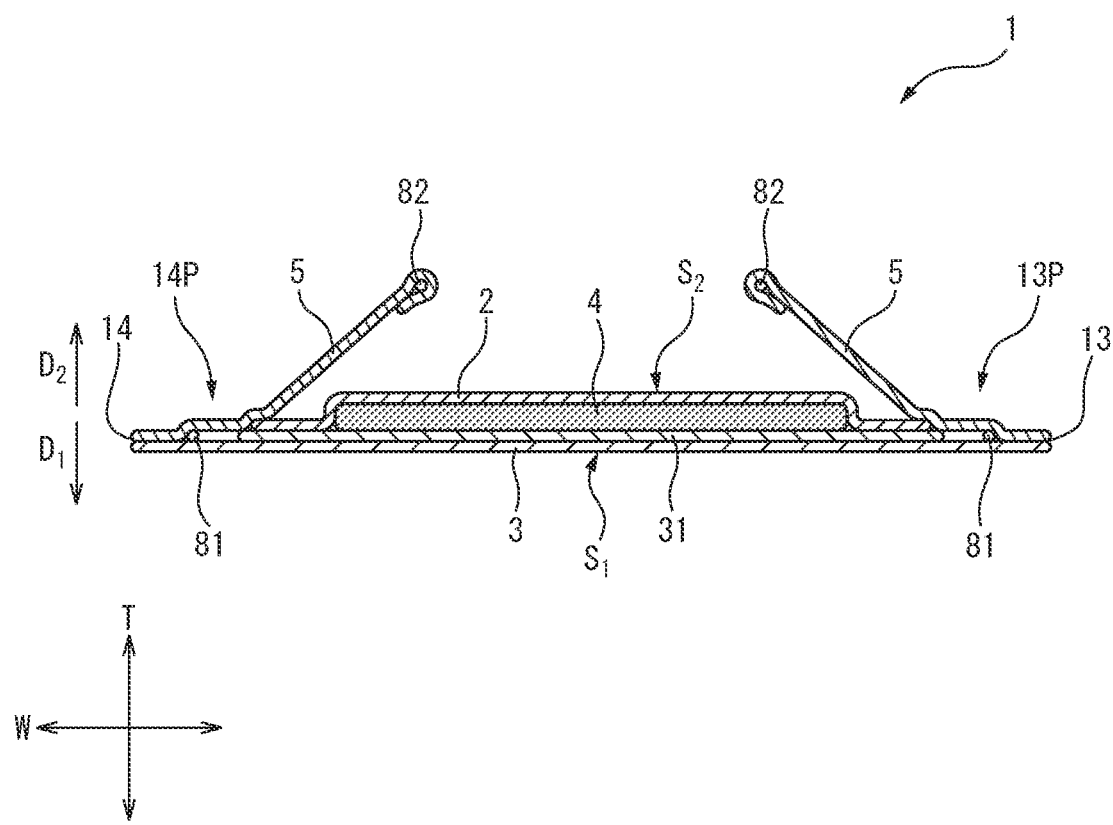
FIG. 4 is an end view of the width direction cross section along the longitudinal direction central axis line $C_W$ which extends in the width direction W of the diaper for pets 1 according to one or more embodiments.
Figure 5:
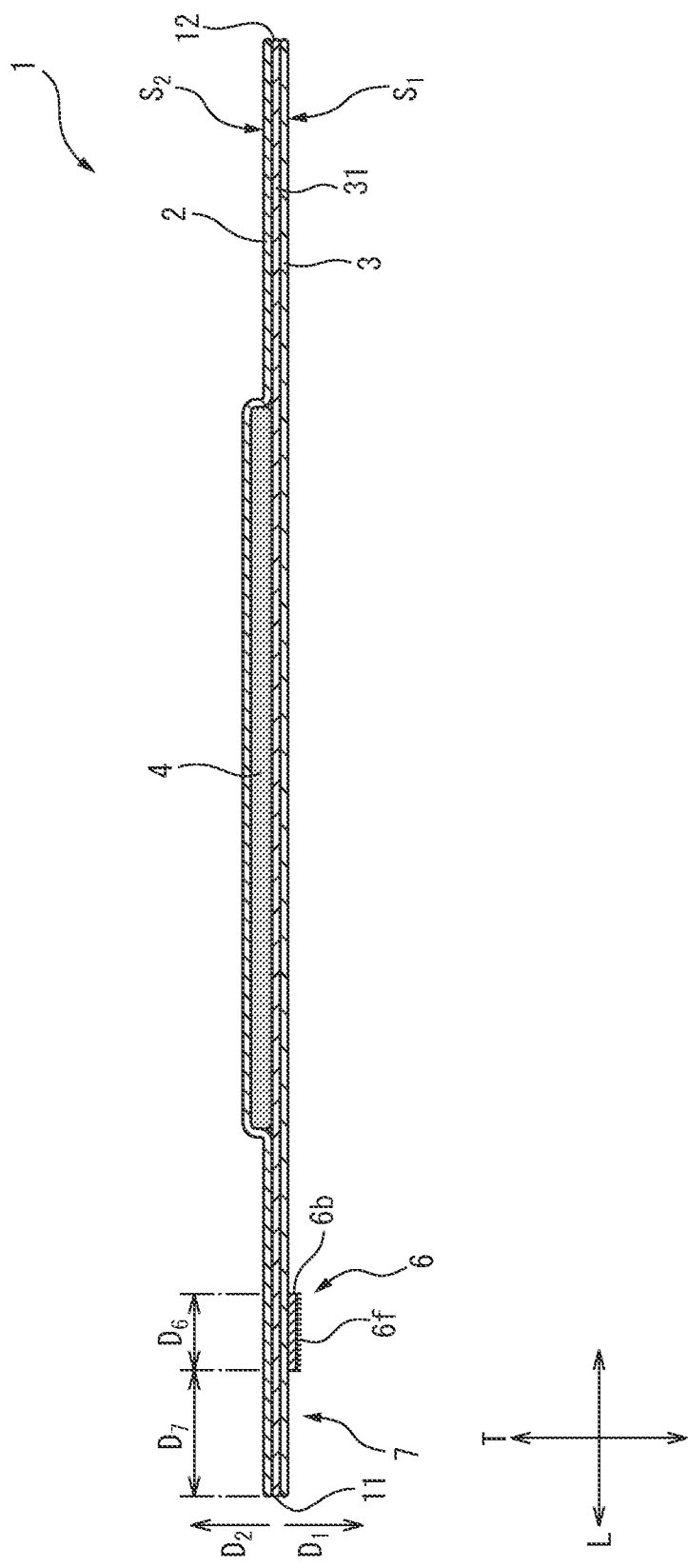
FIG. 5 is an end view of the longitudinal direction cross section along the width direction central axis line $C_L$ which extends in the longitudinal direction L of the diaper for pets 1 according to one or more embodiments.
Figure 6:
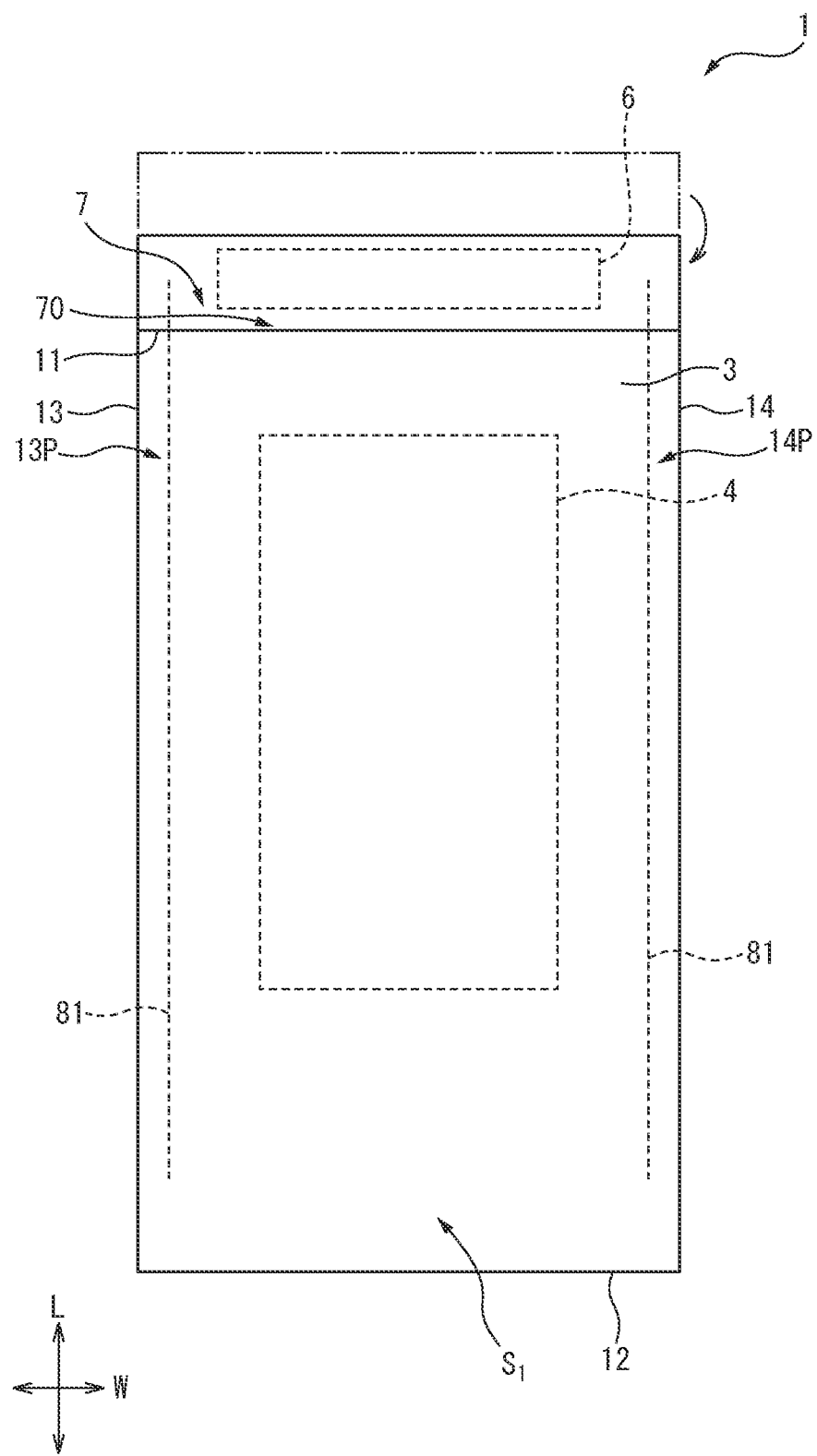
FIG. 6 is a plan view which shows how the flap portion 7 of the diaper for pets 1 is bent toward the first surface side so as to be adhered to the engagement portion 6 according to one or more embodiments.

FIG. 1 is a perspective view of the diaper for pets 1 according to one or more embodiments, FIG. 2 is a plan view of the diaper for pets 1 in an expanded state viewed from the first surface side (the back sheet side) in the thickness direction T, and FIG. 3 is a plan view of the diaper for pets 1 in an expanded state viewed from the second surface side (the top sheet side) in the thickness direction T. Further, FIG. 4 is an end view of the width direction cross section along the longitudinal direction central axis line $C_W$ which extends in the width direction W of the diaper for pets 1, FIG. 5 is an end view of the longitudinal direction cross section along the width direction central axis line $C_L$ which extends in the longitudinal direction L of the diaper for pets 1. Still further, FIG. 6 is a plan view which shows how the flap portion 7 of the diaper for pets 1 is bent toward the first surface side $D_1$ so as to be adhered to the engagement portion 6.

The disposable diaper for pets 1 (which is one example of "the absorbent article for animals" according to the present invention) according to one or more embodiments has, as shown in FIG. 1 to FIG. 3, in a plan view, a longitudinal rectangular outer shape with the longitudinal direction L and the width direction W, and is configured so as to be wound around the waist of an animal in a state in which the longitudinal direction L corresponds to the direction of the waist including the back portion and the abdomen portion of an animal such as a dog, etc. (the waist direction). Incidentally, the diaper for pets 1 according to one or more embodiments has, as shown in FIG. 2, as the outer edges of the rectangular outer shape, one side edge 11 in the longitudinal direction L, the other side edge 12 in the longitudinal direction L, one side edge 13 in the width direction W, and the other side edge 14 in the width direction W.

Further, in one or more embodiments of the present invention, as the outer shape, various sizes, etc., of the absorbent article for animals, arbitrary longitudinal outer shape (for example, a rectangular shape, an oval shape, and an hourglass shape, etc.), and various sizes, etc., can be adopted., as long as they have a long shape which includes a longitudinal direction length that is longer than the length around the torso of the attaching target animal.

The diaper for pets 1 according to one or more embodiments has, as shown in FIG. 1 to FIG. 5, in the thickness direction T, the first surface $S_1$ which is to be the torso non-facing surface, the second surface $S_2$ which is to be the torso facing surface, when being attached to the torso of a pet (an animal), and has the top sheet 2 formed by a nonwoven fabric which forms the second surface $S_2$, the back sheet 3 formed by a nonwoven fabric which forms the first surface $S_1$, and the absorbent body 4 formed by an absorbent member disposed between these sheets, as the basic configuration of the diaper, and is configured so that liquid excrements such as urine, etc., excreted by an animal can be absorbed and retained by the absorbent body 4 while letting such excrements permeate through the top sheet 2 in the thickness direction T.

Further, the diaper for pets 1 has, as shown in FIG. 2 and FIG. 3, in a plan view, between the one side edge 11 and the other side edge 12 in the longitudinal direction L, the first region $A_1$, the center region $A_C$, and the second region $A_2$ which divide the diaper for pets 1 into three equal portions in the longitudinal direction L, and the above described top sheet 2 and the back sheet 3 extend across from the one side edge 11 to the other side edge 12 in the longitudinal direction L, whereas the absorbent body 4 extends across from a portion of the first region $A_1$ to a portion of the second region $A_2$. Incidentally, in the present description, "dividing the absorbent article into three equal portions in the longitudinal direction" means dividing the length between the one side edge and the other side edge in the longitudinal direction into three equal portions, at the width direction central axis line $C_L$ which extends in the longitudinal direction of the absorbent article.

Further, in the present description, the one side edge and the other side edge in the longitudinal direction of the absorbent article for animals means the edges on the one side and the other side which are positioned on the most outer side in the longitudinal direction of the absorbent article for animals, and the same applies to the one side edge and the other side edge in the width direction of the absorbent article for animals.

In this relation, in the present description, the one side end portion and the other side end portion in the longitudinal direction of the absorbent article for animals mean the portions which are defined as the regions that include the one side edge and the other side edge in the longitudinal direction of the absorbent article for animals, extend toward the inner side in the longitudinal direction, respectively, and the longitudinal direction length from each of the edges is or less than 33% of the longitudinal direction whole length (this longitudinal direction whole length is regarded as 100%), and the same applies to the one side end portion and the other side end portion in the width direction of the absorbent article for animals.

Incidentally, the one side edge, the other side edge, the one side end portion, and the other side end portion in various directions are similarly applied to various members and various regions, etc. which configure the absorbent article for animals (for example, the top sheet, the absorbent body, the back sheet, the engagement portion, the compressed portion formation region, etc.).

Incidentally, in the present description, "the one side" and "the other side" in various directions of the various members and various regions, etc. which configure the absorbent article for animals are used so as to correspond to "the one side" and "the other side" in various directions of the absorbent article for animals.

The above described diaper for pets 1 according to one or more embodiments includes, as shown in FIG. 3 to FIG. 5, the back film 31 which is disposed between the absorbent body 4 and the back sheet 3, the pair of side sheets 5, 5 which extend in the longitudinal direction L disposed at each of the both end portions in the width direction W of the diaper for pets 1 at the second surface side $D_2$ of the top sheet 2, and the engagement portion 6 which is disposed so as to extend in the width direction W on the first surface $S_1$ of the above described first region $A_1$ and is capable of being detachably engaged with the second surface $S_2$ of the above described second region $A_2$, and is configured so that the diaper for pets 1 can be steadily attached to the torso of an animal and the liquid excrements such as urine, etc., which is excreted from an animal does not leak outside.

Incidentally, the above described engagement portion 6 is configured, as shown in FIG. 5, by a mechanical fastener which is formed by the belt-like base portion 6b joined to the surface on the first surface side $D_1$ of the back sheet 3 (that is, the first surface $S_1$ of the diaper for pets 1), and the plurality of hook portions 6f (the engagement element) protruded from the base portion 6b, and when the diaper for pets 1 is attached from the abdomen portion side of an animal along the waist, the above described hook portions 6f can be engaged to arbitrary portions of the surface on the second surface side $D_2$ of the top sheet 2 which is formed by a nonwoven fabric (that is, the second surface $S_2$ of the diaper for pets 1), at the back portion side of the animal. By including such an engagement portion 6, the diaper for pets 1 can be attached properly in accordance with the waist size of an animal, at a suitable position of the torso of the animal.

Incidentally, the diaper for pets 1 according to one or more embodiments further includes, as shown in FIG. 1 to FIG. 4, the pair of elastic members for side portion gather formation 81, 81 which extend in the longitudinal direction L disposed between the above described pair of side sheets 5, 5 and the back sheet 3 at each of the both end portions in the width direction W of the diaper for pets 1, and the pair of elastic members for three-dimensional gather formation 82, 82 which extend in the longitudinal direction L disposed at each of the end portions on the inner side in the width direction W of the pair of side sheets 5, 5, and since the predetermined stretching and shrinking property in the longitudinal direction L is added to the whole diaper for pets 1, when attaching the diaper for pets 1 to the torso of an animal, the diaper for pets 1 shrinks in the waist direction of the animal (that is, in the longitudinal direction L in a plan view), so as to be easily in close contact therewith in accordance with the body shape, etc., of an animal. Further, since the diaper for pets 1 which is attached to the torso of an animal is capable of stretching and shrinking in the waist direction of the animal in accordance with the change in waist size, etc., caused by the movement of breathing, etc., of the animal, by the action of each of the above described elastic members, it is easy for the diaper for pets 1 to maintain the state of being attached to the torso of an animal for a long period of time.

Further, the diaper for pets 1 according to one or more embodiments includes, as shown in FIG. 1, FIG. 2, FIG. 5, and FIG. 6, in the longitudinal direction L, the flap portion 7 which extends from the one side edge 61 in the longitudinal direction L of the engagement portion 6 to the one side edge 11 in the longitudinal direction L of the diaper for pets 1, and the flap portion 7 has the longitudinal direction length $D_7$ which is longer than the longitudinal direction length $D_6$ of the engagement portion 6.

In this manner, since in the diaper for pets 1 according to one or more embodiments, the flap portion 7 has the longitudinal direction length $D_7$ which is longer than the longitudinal direction length $D_6$ of the engagement portion 6, even when the flap portion 7 is bent toward the first surface side $D_1$ as described above so as to be adhered to the engagement portion 6 (refer to FIG. 6), by grasping the portion which is longer than the longitudinal direction length $D_6$ of the engagement portion 6 in the flap portion 7 (that is, the surplus portion 70) as the grasping portion, the flap portion 7 can be easily torn off from the engagement portion 6.

Accordingly, by the diaper for pets 1 according to one or more embodiments, it does not take much trouble to be attached to the torso of an animal.

Incidentally, in the absorbent article for animals according to one or more embodiments of the present invention, the longitudinal direction length of the flap portion is not particularly limited as long as it is longer than the longitudinal direction length of the engagement portion, and an arbitrary longitudinal direction length can be adopted in accordance with the desired appearance, and ease of handling, etc.

Further, in the present description, "the longitudinal direction length of the engagement portion" means the longitudinal direction length between the outer side edge which is positioned on the most outer side in the longitudinal direction of the engagement portion and the inner side edge which is positioned on the most inner side in the longitudinal direction of the engagement portion, and for example, in the above described embodiments, corresponds to the longitudinal direction length $D_6$ from the one side edge 61 (the outer side edge) in the longitudinal direction L of the engagement portion 6 to the other side edge 62 (the inner side edge) in the longitudinal direction L of the engagement portion 6.

In the same manner, in the present description, "the longitudinal direction length of the flap portion" means the longitudinal direction length between the edge which is positioned on the most outer side in the longitudinal direction of the engagement portion and the one side edge which is positioned on the most outer side in the longitudinal direction of the absorbent article for animals, and for example, in the above described embodiments, corresponds to the longitudinal direction length $D_7$ from the one side edge 61 in the longitudinal direction L of the engagement portion 6 to the one side edge 11 in the longitudinal direction L of the diaper for pets 1.

Figure 7:
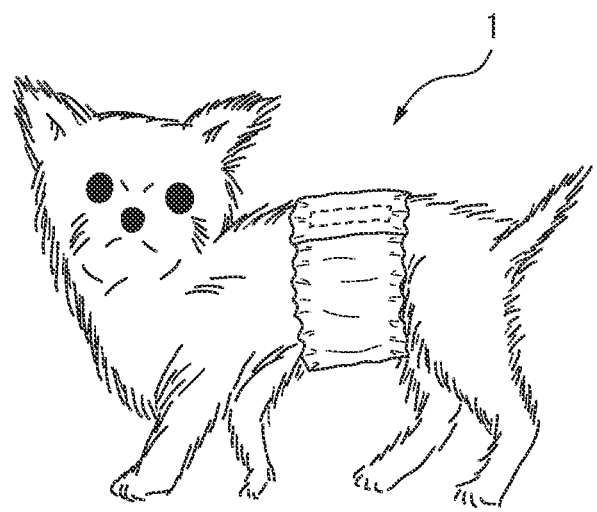
FIG. 7 is a schematic view which shows the state in which the diaper for pets 1 is attached to a male dog according to one or more embodiments.

The diaper for pets 1 according to one or more embodiments is attached to the torso of an animal in the following manner. Incidentally, FIG. 7 is a schematic view which shows the state in which the diaper for pets 1 according to one or more embodiments is attached to a male dog (which is one example of "an animal" according to the present invention).

First, the diaper for pets 1 is applied to the abdomen portion of an animal so that the longitudinal direction L intersects with the back and forth direction of the animal (that is, the width direction W corresponds to the back and forth direction of the animal), and the absorbent body 4 faces the excretion portion (the urethral opening) of the animal. Further, the diaper for pets 1 which has been applied to the abdomen portion of the animal is wound around the torso from the abdomen portion along the waist of the animal. At this time, the second region $A_2$ of the diaper for pets 1 is overlapped on the first surface $S_1$ of the first region $A_1$, so as to be engaged and fixed by the engagement portion 6 which is disposed on the first surface $S_1$ of the first region $A_1$. In this manner, the diaper for pets 1 is attached to the torso of an animal as shown in FIG. 7.

"The animal" to which the absorbent article for animals according to one or more embodiments of the present invention is applied is not particularly limited as long as it is a quadruped animal (a four-limb animal) with an excretion organ in the abdomen portion, and other than a dog (a male dog) as in the above described embodiments, for example, various animals such as a male horse, etc., may be targeted.

Further, the liquid excrements which is the target of the absorption and retention of the absorbent article for animals according to one or more embodiments of the present invention is not particularly limited, and for example, various bodily fluid which is liquid or has low viscosity such as urine, blood, etc., may be mentioned.

Hereinbelow, various members which configure the absorbent article for animals according to one or more embodiments are explained in further detail by using the diaper for pets 1 according to the above described embodiments, etc.

[Top Sheet]

In the diaper for pets 1 according to one or more embodiments, the top sheet 2 has, as shown in FIG. 3 to FIG. 5, in a plan view, a longitudinal rectangular outer shape which extends in the longitudinal direction L and in the width direction W of the diaper for pets 1, is disposed at a position which forms the second surface $S_2$ that is to be the torso facing surface of the diaper for pets 1, in the thickness direction T of the diaper for pets 1, and is formed by a liquid permeable nonwoven fabric which receives liquid excrements such as urine, etc., excreted from an animal of the attaching target. That is, in one or more embodiments, the top sheet 2 is formed by a nonwoven fabric which forms the second surface $S_2$ of the diaper for pets 1.

Incidentally, in the diaper for pets 1 according to one or more embodiments, the first surface $S_1$ which has the above described engagement portion 6 is the torso non-facing surface, and the second surface $S_2$ is the torso facing surface (that is, the nonwoven fabric which forms the first surface $S_1$ is the back sheet 3, and the nonwoven fabric which forms the second surface $S_2$ is the top sheet 2), however, the absorbent article for animals according to embodiments of the present invention is not limited to such an aspect, and an aspect in which the first surface which has the engagement portion is the torso facing surface, and the second surface is the torso non-facing surface (that is, the nonwoven fabric which forms the first surface is the top sheet, and the nonwoven fabric which forms the second surface is the back sheet) may be applied. That is, whichever of these aspects is applied to the absorbent article for animals according to one or more embodiments of the present invention, each of the top sheet and the back sheet is formed by a nonwoven fabric (and to be more specific, either one of the nonwoven fabric which forms the first surface and the nonwoven fabric which forms the second surface).

In one or more embodiments, the nonwoven fabric to be used for the top sheet is not particularly limited as long as it has certain properties applicable to the top sheet of an absorbent article for animals (for example, the liquid permeability, the softness, etc.), and for example, an arbitrary nonwoven fabric such as a spunlace nonwoven fabric, an air through nonwoven fabric, a spunbond nonwoven fabric, a point bond nonwoven fabric, a meltblown nonwoven fabric, and a combination of the above described (for example, an SMS nonwoven fabric, etc.), etc., may be used.

Further, the configuration of such a nonwoven fabric is not particularly limited, and other than a flat non-porous nonwoven fabric, for example, a perforated nonwoven fabric, a nonwoven fabric which has a protruded and recessed structure (a protruded and recessed structure or a ridge and groove structure, etc., with the cross sectional shape being wavy), etc., may also be preferably used.

Further, the types of the configurational fibers of the nonwoven fabric are not particularly limited, and for example, cellulose fibers; hydrophilic fibers such as thermoplastic resin fibers, etc., such as olefin resins and polyester resins, etc., that have been subjected to hydrophilization treatment may be mentioned, and these fibers may be used alone or in combination of two or more types of fibers.

In one or more embodiments, the outer shape and various sizes, etc., of the nonwoven fabric to be used for the top sheet are not particularly limited as long as they can cover at least the surface on the torso facing surface side of the absorbent body, and an arbitrary outer shape in accordance with the type, the body shape, the size, etc., of the attaching target animal (for example, an hourglass shape, an oval shape, etc.) and various sizes, etc., may be adopted. For example, the thickness of the nonwoven fabric to be used for the top sheet may adopt the thickness within the range of 0.001 mm to 5.0 mm, however, from the viewpoint of the liquid permeability the softness, the thickness within the range of 0.01 mm to 3.0 mm is preferable, and further, the thickness within the range of 0.1 mm to 1.0 mm is more preferable.

Incidentally, the basis weight of the nonwoven fabric to be used for the top sheet is also not particularly limited. For example, in one or more embodiments, the basis weight may be within the range of 5 $g/m^2$ to 100 $g/m^2$. However, from the viewpoint of the liquid permeability and the softness, the basis weight may be within the range of 6 $g/m^2$ to 50 $g/m^2$ in one or more embodiments. Incidentally, the basis weight of the nonwoven fabric can be measured in accordance with 5.2 of JIS L 1906.

[Absorbent Body]

In the diaper for pets 1 according to the above described embodiments, the absorbent body 4 has, as shown in FIG. 2 to FIG. 5, in a plan view, a longitudinal rectangular outer shape as a whole, which extends in the longitudinal direction L and the width direction W of the diaper for pets 1, is disposed between the top sheet 2 and the back sheet 3 in the thickness direction T of the diaper for pets 1, and is formed by an absorbent member which is capable of absorbing and retaining liquid excrements such as urine of an animal, etc., which has permeated through the top sheet 2. The absorbent body 4 is disposed, as shown in FIG. 2 and FIG. 3, in a plan view, having the center portion in which the longitudinal direction central axis line $C_W$ which extends in the width direction W of the diaper for pets 1 and the width direction central axis line $C_L$ which extends in the longitudinal direction L intersects with each other as the center, and in the longitudinal direction L, extends from a portion of the first region $A_1$ to a portion of the second region $A_2$.

In one or more embodiments, the absorbent member to be used for the absorbent body is not particularly limited as long as it has certain properties applicable to the absorbent body of an absorbent article for animals (for example, the absorbency, the liquid retainability, the softness, the strength, etc.), and an arbitrary absorbent member known in the art may be used. As an example of such an absorbent member, an absorbent core which is formed by absorbent materials including absorbent fibers such as pulp, etc., and/or super absorbent polymers (SAP), being covered by at least one liquid permeable cover sheet which has hydrophilicity (for example, tissue, etc.), may be mentioned.

In one or more embodiments, the outer shape and various sizes, etc., of the absorbent member to be used for the absorbent body are not particularly limited as long as they are capable of absorbing and retaining liquid excrements such as urine, etc., excreted by an animal, and an arbitrary outer shape in accordance with the type, the body shape, the size, etc., of the attaching target animal (for example, an hourglass shape, an oval shape, etc.) and various sizes, etc., may be adopted.

Incidentally, the thickness and the basis weight, etc., of the absorbent member to be used for the absorbent body are also not particularly limited as long as they are applicable to be used for the absorbent body of an absorbent article for animals, and an arbitrary thickness, and basis weight, etc., in accordance with the type, the body shape, the size, etc., of the attaching target animal may be adopted.

[Back Film]

In the diaper for pets 1 according to the above described embodiments, the back film 31 (which is one example of "the liquid impermeable member" in the present invention) has, in a plan view, a longitudinal rectangular outer shape, which extends in the longitudinal direction L and the width direction W of the diaper for pets 1, is disposed, as shown in FIG. 4 and FIG. 5, between the absorbent body 4 and the back sheet 3 in the thickness direction T of the diaper for pets 1, and is formed by a sheet-like liquid impermeable member which prevents the liquid excrements such as urine, etc., that has permeated through the above described top sheet 2 and the absorbent body 4 from leaking outside of the diaper for pets 1.

In one or more embodiments, the sheet-like liquid impermeable member to be used for the back film is not particularly limited as long as it has certain properties applicable to the back film of an absorbent article for animals (for example, the liquid impermeability, the softness, the strength, etc.), and an arbitrary sheet-like liquid impermeable member known in the art may be used. As an example of such a sheet-like liquid impermeable member, for example, a liquid impermeable plastic film, a hydrophobic nonwoven fabric, an SMS laminated nonwoven fabric, and a laminated sheet in which these sheets are arbitrarily combined, etc., may be mentioned.

In one or more embodiments, the outer shape and various sizes, etc., of the sheet-like liquid impermeable member to be used for the back film are not particularly limited as long as they are capable of covering at least the surface on the torso non-facing surface side of the absorbent body, and an arbitrary outer shape in accordance with the type, the body shape, the size, etc., of the attaching target animal and various sizes, etc., may be adopted.

Incidentally, since providing such a back film (the sheet-like liquid impermeable member) to the absorbent article for animals is not a mandatory configurational requirement, in a case in which the leakage prevention of the liquid excrements is secured by an additional liquid impermeable back sheet or absorbent body, etc., the absorbent article for animals according to one or more embodiments of the present invention does not have to include such a back film.

[Back Sheet]

In the diaper for pets 1 according to the above described embodiments, the back sheet 3 has, as shown in FIG. 2 to FIG. 5, in a plan view, a longitudinal rectangular outer shape, which extends in the longitudinal direction L and the width direction W of the diaper for pets 1, is disposed at a position of forming the first surface $S_1$ which is to be the torso non-facing surface of the diaper for pets 1 in the thickness direction T of the diaper for pets 1, and is formed by a liquid impermeable nonwoven fabric which prevents the liquid excrements such as urine, etc., that has been excreted from an animal to be the attaching target from leakage. That is, in one or more embodiments, the back sheet 3 is formed by a nonwoven fabric which forms the first surface $S_1$ of the diaper for pets 1.

In one or more embodiments, the nonwoven fabric to be used for the back sheet is not particularly limited as long as it has certain properties applicable to the back sheet of an absorbent article for animals (for example, the liquid impermeability, the air permeability, the softness, etc.), and for example, an arbitrary nonwoven fabric such as an SMS nonwoven fabric, a spunbond nonwoven fabric, a point bond nonwoven fabric, a meltblown nonwoven fabric which are formed by waterproof or hydrophobic synthetic resin fibers, a nonwoven fabric configured by ultrafine fibers with a fineness of 1 dtex or less, a nonwoven fabric which includes a fiber layer configured by ultrafine fibers, and a nonwoven fabric which has been subjected to densification treatment by adding heat or pressure, etc., may be used, and further, a nonwoven fabric laminated sheet in which an arbitrary nonwoven fabric is laminated on at least one surface of a liquid impermeable plastic film, etc., may also be used.

Further, the configuration of such a nonwoven fabric is not particularly limited, and other than a flat non-porous nonwoven fabric, for example, a perforated nonwoven fabric, a nonwoven fabric which has a predetermined protruded and recessed structure (a protruded and recessed structure or a ridge and groove structure, etc., with the cross sectional shape being wavy), etc., may also be preferably used.

Further, the types of the configurational fibers of the nonwoven fabric are also not particularly limited, and for example, fibers formed by olefin-based resin such as polyethylene and polypropylene, etc.; fibers formed by polyester-based resin such as polyethylene terephthalate, etc.; hydrophobic thermoplastic resin fibers such as composite fibers, etc., may be mentioned, and these fibers may be used alone or in combination of two or more types of fibers.

In one or more embodiments, the outer shape and various sizes, etc., of the nonwoven fabric to be used for the back sheet are not particularly limited as long as they are capable of covering at least the surface on the torso non-facing surface side of the absorbent body, and an arbitrary outer shape in accordance with the type, the body shape, the size, etc., of the attaching target animal (for example, an hourglass shape, an oval shape, etc.) and various sizes, etc., may be adopted. For example, the thickness of the nonwoven fabric to be used for the back sheet may adopt the thickness within the range of 0.001 mm to 5.0 mm, however, from the viewpoint of the liquid impermeability, the softness, and the air permeability, etc., the thickness within the range of 0.003 mm to 3.0 mm is preferable, and further, the thickness within the range of 0.01 mm to 1.0 mm is more preferable.

Incidentally, the basis weight of the nonwoven fabric to be used for the back sheet is also not particularly limited. For example, in one or more embodiments, the basis weight may be within the range of 5 $g/m^2$ to 100 $g/m^2$. However, from the viewpoint of the liquid impermeability and the softness, the basis weight may be within the range of 6 $g/m^2$ to 50 $g/m^2$ in one or more embodiments.

[Side Sheets]

In the diaper for pets 1 according to the above described embodiments, the pair of side sheets 5, 5 are disposed, as shown in FIG. 3 and FIG. 4, so as to be positioned on the torso facing surface side (that is, the second surface side $D_2$) of the top sheet 2 and extend in the longitudinal direction L at each of the both end portions in the width direction W of the diaper for pets 1.

Each of the pair of side sheets 5, 5 is formed, in a plan view, by a belt-like hydrophobic sheet member which is long in the longitudinal direction L, and further, in each of the pair of side sheets 5, 5, as shown in FIG. 4, the surface on the torso non-facing surface side (that is, the first surface side $D_1$) of the end portion on the outer side in the width direction W is joined respectively to the surface on the torso facing surface side (that is, the second surface side $D_2$) of the top sheet 2 and the back sheet 3, whereas the surface on the torso non-facing surface side of the end portion on the inner side in the width direction W is not joined to any of the sheet members (for example, the top sheet 2, and the back sheet 3, etc.).

Further, in each of the above described pair of side sheets 5, 5, as shown in FIG. 4, the end portion on the inner side in the width direction W is folded toward the top sheet 2 side, and further, the pair of elastic members for three-dimensional gather formation 82, 82 which extend in the longitudinal direction L are disposed so as to be sandwiched between the folded end portion. By the shrinkage of the pair of elastic members for three-dimensional gather formation 82, 82 in the longitudinal direction L, the end portions on the inner side in the width direction W of the pair of side sheets 5, 5 (the free end portions) stand up from the top sheet 2 side, and can form the three-dimensional gather as shown in FIG. 4. Since in the diaper for pets 1 according to one or more embodiments, such a three-dimensional gather functions as a leakage prevention wall, and it is difficult for the liquid excrements, etc., such as urine excreted from an animal to leak out.

Incidentally, in the above described embodiments, as shown in FIG. 4, in the both end portions in the width direction W of the diaper for pets 1, the pair of elastic members for side portion gather formation 81, 81 which extend in the longitudinal direction L are disposed between the pair of side sheets 5, 5 and the back sheet 3. Such pair of elastic members for side portion gather formation 81, 81 will be described later.

In one or more embodiments, the number of the elastic members for three-dimensional gather formation is not particularly limited. In one or more embodiments, one or two or more elastic members may be disposed on each of the pair of the side sheets, or one or two or more elastic members may be disposed on either one of the side sheets.

Incidentally, the elastic members for three-dimensional gather formation is not particularly limited as long as it can add the shrinking force in the longitudinal direction to the absorbent article for animals in an expanded state, and an arbitrary elastic member may be used in the same manner as the elastic members for side portion gather formation which will be described later.

In one or more embodiments, the belt-like hydrophobic sheet member to be used for the side sheets is not particularly limited as long as it can function as the above described leakage prevention wall, and for example, an arbitrary nonwoven fabric with a water repellent property or a hydrophobic property (for example, a spunlace nonwoven fabric, a spunbond nonwoven fabric, a thermal bond nonwoven fabric, a meltblown nonwoven fabric, an air through nonwoven fabric, etc.) being cut into a belt-like shape may be used. Further, the configurational fibers of such a nonwoven fabric is also not particularly limited, and for example, synthetic fibers such as olefin-based resin fibers, polyester-based resin fibers, polyamide-based resin fibers, etc., and cellulose-based fibers such as rayon, cotton, etc., may also be used.

Incidentally, in one or more embodiments, the outer shape and various sizes, etc., of each of the pair of side sheets are not particularly limited as long as they are applicable to be used for the side sheets of an absorbent article for animals, and an arbitrary outer shape and various sizes, etc., in accordance with the type, the body shape, the size, etc., of the attaching target animal may be adopted.

Further, since providing such a pair of side sheets to the absorbent article for animals is not a mandatory configurational requirement, in a case in which the leakage prevention of the liquid excrements is secured by another configurational member, etc., the absorbent article for animals according to one or more embodiments of the present invention does not have to include such a pair of side sheets.

(Elastic Members for Side Portion Gather Formation)

In the diaper for pets 1 according to the above described embodiments, the pair of elastic members for side portion gather formation 81, 81, as shown in FIG. 2 to FIG. 4, are disposed between the pair of side sheets 5, 5 and the back sheet 3 so as to extend in the longitudinal direction L at each of the both end portions in the width direction W of the diaper for pets 1, and are formed by stretchable and shrinkable thread-like elastic members which are capable of adding the shrinking force in the longitudinal direction L to the diaper for pets 1 which is in an expanded state.

By such elastic members for side portion gather formation 81, 81 being disposed at both end portions in the width direction W of the diaper for pets 1, the both end portions in the width direction W of the diaper for pets 1 when being attached (that is, the back and forth direction of an animal when being attached) can be made to be in close contact along the waist of the animal more precisely, the leakage of the liquid excrements such as urine, etc., excreted from an animal can be made to be difficult more reliably.

In one or more embodiments, the elastic member which is applicable to the elastic members for side portion gather formation is not particularly limited as long as it can add the shrinking force in the longitudinal direction to the absorbent article for animals in an expanded state, and for example, an arbitrary elastic members such as a thread rubber or a flat rubber formed by natural rubber; stretching and shrinking molded body in which thermoplastic elastomers such as urethane and ethylene-vinyl acetate copolymer (EVA), etc., are molded into a thread-like shape or a belt-like shape; stretching and shrinking sheet-like member such as a stretching and shrinking nonwoven fabric, etc., may be used.

Incidentally, in one or more embodiments, the disposing manner of the elastic members for side portion gather formation is not limited to the aspect of the above described embodiments, and the elastic members for side portion gather formation may be disposed in accordance with the type, the body shape, the size, etc., of the attaching target animal, and for example one or two or more elastic members may be disposed at only one end portion among the both end portions in the width direction of the absorbent article for animals, or alternatively, two or more elastic members may be disposed at each of the both end portions in the width direction of the absorbent article for animals (that is, four or more elastic members in total).

Incidentally, since providing such elastic members for side portion gather formation to the absorbent article for animals is not a mandatory configurational requirement, in a case in which the close contact with the torso of an animal and the leakage prevention of the liquid excrements are secured by another configurational member, etc., the absorbent article for animals according to one or more embodiments of the present invention does not have to include such elastic members for side portion gather formation.

[Engagement Portion]

In the diaper for pets 1 according to the above described embodiments, the engagement portion 6 is disposed, as shown in FIG. 2, so as to extend in the width direction W on the first surface $S_1$ of the above described first region $A_1$ (to be more specific, on the surface of the first surface side $D_1$ of the back sheet 3) and in a plan view, has a rectangular outer shape which is long in the width direction W of the diaper for pets 1 that includes the one side edge 61 in the longitudinal direction L positioned on the outer side in the longitudinal direction L, the other side edge 62 in the longitudinal direction L positioned on the inner side in the longitudinal direction L, the one side edge 63 in the width direction W positioned on one side in the width direction W, and the other side edge 64 in the width direction W positioned on the other side in the width direction W.

Such an engagement portion 6 is configured, as shown in FIG. 5, by a mechanical fastener which includes the belt-like base portion 6b that is long in the width direction W of the diaper for pets 1 joined to the surface of the first surface side $D_1$ of the back sheet 3, and the plurality of hook portions 6f (the engagement element) that protrude from the base portion 6b, and in such a mechanical fastener, the above described plurality of hook portions 6f are capable of being engaged to the configurational fibers of the nonwoven fabric, whereby when attaching the diaper for pets 1 from the abdomen portion side of an animal along the waist, the above described hook portions 6f can be engaged to arbitrary portions of the surface on the second surface side $D_2$ of the top sheet 2 which is formed by a nonwoven fabric, at the back portion side of the animal.

Incidentally, in the present description, "the engagement" means the state in which elements which have predetermined structures are mechanically attached so as to be connected to each other, and the connected state is maintained unless each of the elements are pulled apart with a predetermined force.

In one or more embodiments, the mechanical fastener to be used for the engagement portion is not particularly limited as long as it is capable of being engaged to an arbitrary portion of the nonwoven fabric which forms the second surface, and for example, a mushroom type fastener which includes a flat sheet-like base portion, and hook portions consisted of a plurality of mushroom type engagement protrusions which protrude in the vertical direction from the base portion (that is, shaft portions which protrude in the vertical direction from the base portion, and engagement protrusions which have enlarged diameter portions expanded in the direction in which the outer peripheral surface of the shaft portions expand at the tip of the shaft portions (to be more specific, the tip of the shaft portions on the opposite side of the base portion)); a key type fastener which includes a flat sheet-like base portion, and hook portions consisted of a plurality of key type engagement protrusions which protrude in the vertical direction from the base portion (that is, the engagement protrusions having the structure in which the tip of the shaft portions which protrude in the vertical direction from the base portion being folded back toward the base portion side), etc., may be used.

Among these, in a case in which the mushroom type fastener is used for the engagement portion, when the engagement portion is engaged to the nonwoven fabric which forms the second surface, even when the portion which is engaged to the nonwoven fabric is pulled in various directions by the movement of an animal, etc., the hook portions consisted of the above described mushroom type engagement protrusions can maintain the engaged state with the nonwoven fabric in response to the forces in all directions, whereby the engaged state of the engagement portion and the nonwoven fabric which forms the second surface can be maintained strongly, and as a result, it is difficult for the absorbent article for animals to be shifted from the proper position of the waist of the animal, and to come off from the torso of the animal.

In one or more embodiments, the configurational material of the mechanical fastener to be used for the engagement portion is not particularly limited, and for example, arbitrary synthetic resin such as polyester, polyolefin, polyamide, polyvinyl chloride, olefin-based elastomer, urethane-based elastomer, etc., may be used, and these synthetic resins may be used alone or in combination of two or more types of resins.

Further, as described above, the absorbent article for animals according to one or more embodiments of the present invention may take the aspect in which the first surface including the engagement portion is the torso facing surface, and the second surface is the torso non-facing surface (that is, the nonwoven fabric which forms the first surface is the top sheet, and the nonwoven fabric which forms the second surface is the back sheet), and in the case of such an aspect, the engagement portion is disposed on the surface on the first surface side (that is, the torso facing surface) of the top sheet.

Incidentally, in one or more embodiments, the outer shape, various sizes, etc., of the mechanical fastener to be used for the engagement portion are not particularly limited. In one or more embodiments, an arbitrary outer shape in accordance with the type, the body shape, the size, etc., of the attaching target animal (for example, one or a plurality of squares, rectangular shapes, oval shapes, diamond shapes, etc.), and various sizes, etc., may be adopted. However, as described above, it is required that the longitudinal direction length of the engagement portion (that is, the longitudinal direction length from the one side edge of the engagement portion in the longitudinal direction of the absorbent article for animals (the outer side edge) to the other side edge (the inner side edge)) is shorter than the longitudinal direction length of the flap portion in the absorbent article for animals.

In this manner, the longitudinal direction length of the engagement portion is shorter than the longitudinal direction length of the flap portion in the absorbent article for animals, that is, the longitudinal direction length of the flap portion in the absorbent article for animals is longer than the longitudinal direction length of the engagement portion, whereby in the absorbent article for animals according to one or more embodiments of the present invention, even when the flap portion is bent toward the first surface side as described above so as to be adhered to the engagement portion, by grasping the portion which is longer than the longitudinal direction length of the engagement portion in the flap portion (that is, the surplus portion) as the grasping portion, the flap portion can be easily torn off from the engagement portion.

Accordingly, the absorbent article for animals according to one or more embodiments of the present invention can make it possible so that it does not take much trouble to be attached to the torso of an animal.

Incidentally, in the absorbent article for animals according to one or more embodiments, as described above, the configuration of the engagement portion is not limited to the aspect in the above described embodiments. In one or more embodiments, an arbitrary configuration can be adopted.

Hereinbelow, other embodiments of the present invention in which only the configuration of the engagement portion is different from that in the above described embodiments are explained with reference to the drawings. Incidentally, the configurations other than those different from the above described embodiments are basically the same as those in the above described embodiments, and thus the explanations thereof will be omitted.

Figure 8:
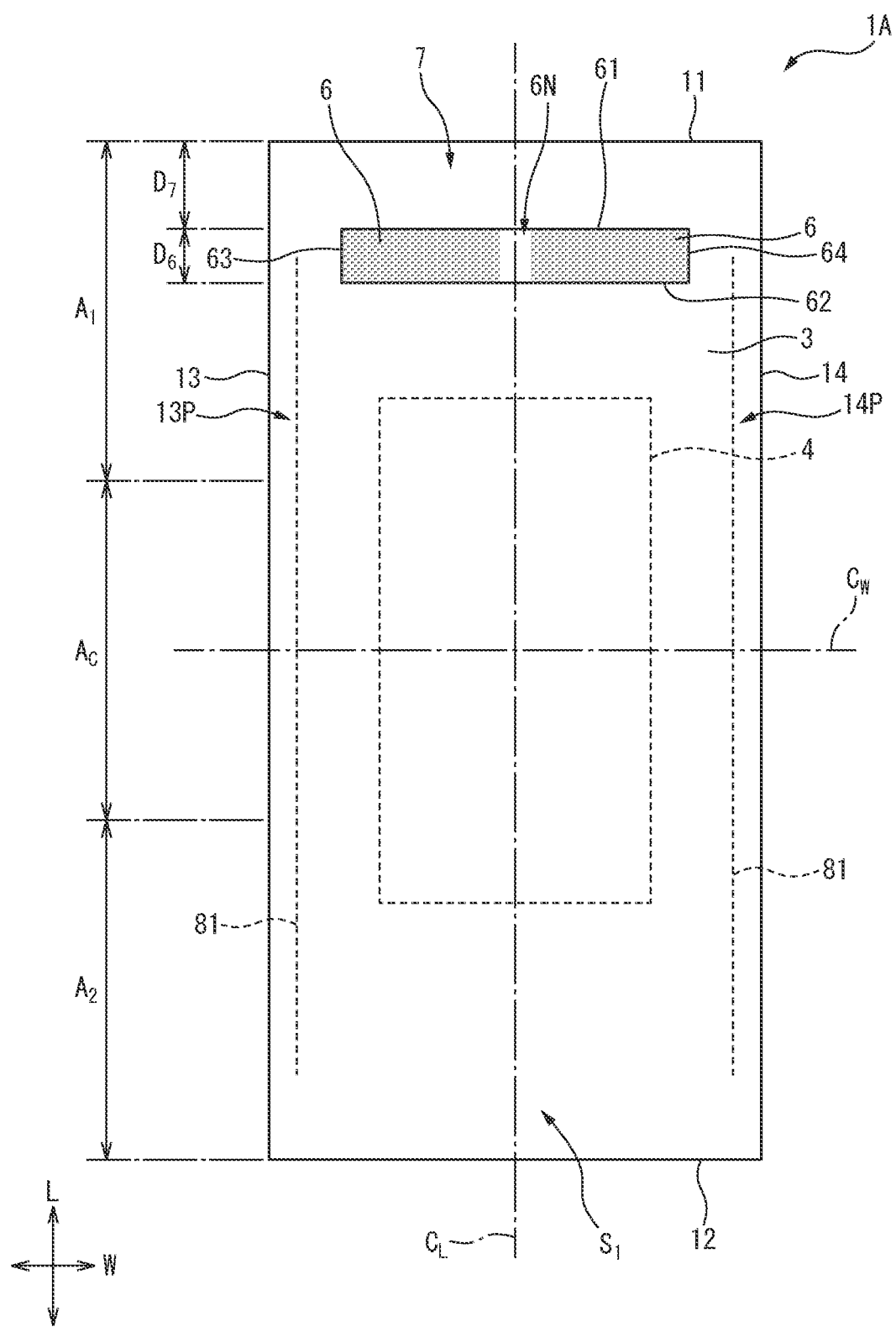
FIG. 8 is a plan view of the diaper for pets 1A according to one or more embodiments in an expanded state viewed from the first surface side in the thickness direction T.

FIG. 8 is a plan view of the diaper for pets 1A according to one or more embodiments in an expanded state viewed from the first surface side $D_1$ in the thickness direction T.

In the diaper for pets 1A according to one or more embodiments, as shown in FIG. 8, the engagement portion 6 includes the engagement element non-disposed portion 6N in which the hook portions 6f as the engagement element are not disposed at the center portion in the width direction W which overlaps with the width direction central axis line $C_L$ that extends in the longitudinal direction L.

Incidentally, in one or more embodiments, the position at which such an engagement element non-disposed portion is provided is not limited to the center portion of the above described width direction, and the engagement element non-disposed portion may be provided at an arbitrary position as long as it is provided at a portion in the width direction of the engagement portion.

In this manner, when the engagement portion includes the engagement element non-disposed portion in which the engagement element is not disposed in a portion in the width direction, even when the flap portion has been bent toward the first surface side so as to be adhered to the engagement portion, the engagement element non-disposed portion can function as the grasping portion together with the above described surplus portion, whereby a wider area of the grasping portion can be secured, and as a result, the flap portion can be even more easily torn off from the engagement portion.

In one or more embodiments, the width direction length of the above described engagement element non-disposed portion is not particularly limited as long as the engagement portion can demonstrate the necessary engagement force (the joining strength) as the engagement portion of the absorbent article for animals, and an arbitrary width direction length may be adopted, however, from the viewpoint of more reliably obtaining the function as the above described grasping portion, the engagement element non-disposed portion preferably has the width direction length capable of allowing the finger of the attacher such as the keeper of the animal, etc., to be inserted therein (for example, the length within the range of 6 mm to 20 mm, etc.).

Further, in one or more embodiments, the disposing manner of the engagement element non-disposed portion is also not particularly limited, as long as the engagement portion can demonstrate the necessary engagement force as the engagement portion of the absorbent article for animals, and for example, the engagement element non-disposed portion may be disposed at the position including at least one edge of the one side edge and the other side edge in the above described width direction of the engagement portion, in addition to the center portion of the above described width direction, or instead of the center portion.

When the engagement element non-disposed portion which is capable of functioning as the grasping portion is disposed at such a position (that is, at the position including at least one edge of the one side edge and the other side edge in the width direction of the engagement portion), when tearing off the flap portion from the engagement portion by grasping the engagement element non-disposed portion as well as the above described surplus portion as the grasping portion, the flap portion can be torn off sequentially from the one side edge or the other side edge in the width direction of the engagement portion, whereby the flap portion can be torn off from the engagement portion with less force compared to the case of tearing the flap portion from the one side edge in the longitudinal direction.

Next, the diaper for pets 1B according to one or more embodiments is explained with reference to the drawings.

Figure 9:
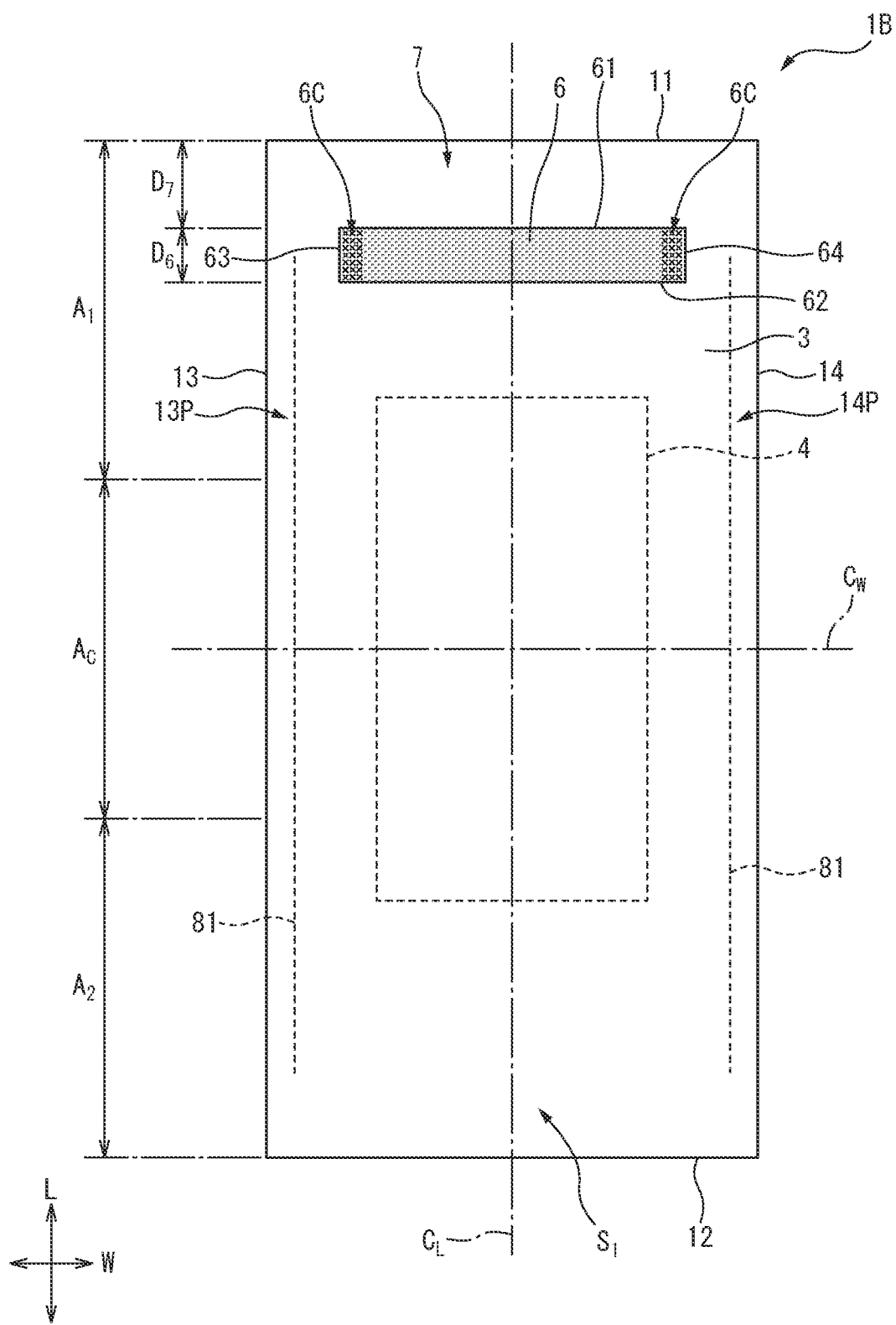
FIG. 9 is a plan view of the diaper for pets 1B according to one or more embodiments in an expanded state viewed from the first surface side in the thickness direction T.

FIG. 9 is a plan view of the diaper for pets 1B according to one or more embodiments in an expanded state viewed from the first surface side $D_1$ in the thickness direction T.

In the diaper for pets 1B according to one or more embodiments, as shown in FIG. 9, the engagement portion 6 includes, at each of the one side end portion including the one side edge 63 in the width direction W and the other side end portion including the other side edge 64 in the width direction W, the engagement element crushed portion 6C which is formed by crushing the hook portions 6f (the engagement element).

Incidentally, in one or more embodiments, the position at which such an engagement element crushed portion is provided is not limited to the both end portions in the above described width direction, and the engagement element crushed portion may be provided at an arbitrary position as long as it is provided at a portion in the width direction of the engagement portion.

In this manner, when the engagement portion includes the engagement element crushed portion which is formed by crushing the engagement element in a portion in the width direction, even when the flap portion has been bent toward the first surface side so as to be adhered to the engagement portion, the engagement element crushed portion can function as the grasping portion together with the above described surplus portion, whereby a wider area of the grasping portion can be secured, and as a result, the flap portion can be even more easily torn off from the engagement portion.

Further, since, although slightly, such an engagement element crushed portion is capable of being more engaged to the nonwoven fabric, compared to the above described engagement element non-disposed portion, there is also an advantage of easily securing a certain or more engagement force in the engagement portion as a whole.

In one or more embodiments, the width direction length of the above described engagement element crushed portion is not particularly limited as long as the engagement portion can demonstrate the necessary engagement force as the engagement portion of the absorbent article for animals, and an arbitrary width direction length may be adopted, however, from the viewpoint of more reliably obtaining the function as the above described grasping portion, the engagement element crushed portion preferably has the width direction length capable of allowing the finger of the attacher such as the keeper of the animal, etc., to be inserted therein (for example, the length within the range of 6 mm to 20 mm, etc.).

Further, in one or more embodiments, the disposing manner of the engagement element crushed portion is also not particularly limited, as long as the engagement portion can demonstrate the necessary engagement force as the engagement portion of the absorbent article for animals, and for example, the engagement element crushed portion may be disposed at an arbitrary position such as at only one end portion in the width direction or at the center portion in the width direction, etc., in addition to the both end portions of the above described width direction, or instead of the both end portions, however, as in the above described embodiments, the engagement element crushed portion is preferably disposed at the position which includes at least one edge of the one side edge and the other side edge in the width direction of the engagement portion.

When the engagement element crushed portion which is capable of functioning as the grasping portion is disposed at such a position (that is, at the position including at least one edge of the one side edge and the other side edge in the width direction of the engagement portion), when tearing off the flap portion from the engagement portion by grasping the engagement element crushed portion as well as the above described surplus portion as the grasping portion, the flap portion can be torn off sequentially from the one side edge or the other side edge in the width direction of the engagement portion, whereby the flap portion can be torn off from the engagement portion with less force compared to the case of tearing the flap portion from the one side edge in the longitudinal direction.

In one or more embodiments, the forming means of the engagement element crushed portion in the engagement portion is not particularly limited, and the engagement element crushed portion may be formed by crushing the engagement element at the predetermined portion in the engagement portion by using a known and arbitrary heated or unheated pressuring means.

Incidentally, in one or more embodiments, the engagement portion may include both of the engagement element non-disposed portion and the engagement element crushed portion according to the above described embodiments.

Further, in the absorbent article for animals according to one or more embodiments of the present invention, the aspect of each of the various configurational members other than the engagement portion is not limited to the aspect in the above described embodiments. In one or more embodiments, an arbitrary aspect may be adopted.

Hereinbelow, other embodiments of the present invention in which the aspects of various configurational members other than the engagement portion are different from those in the above described embodiments are explained with reference to the drawings. Incidentally, the configurations other than those different from the above described embodiments are basically the same as those in the above described embodiments, and thus the explanations thereof will be omitted.

Figure 10:
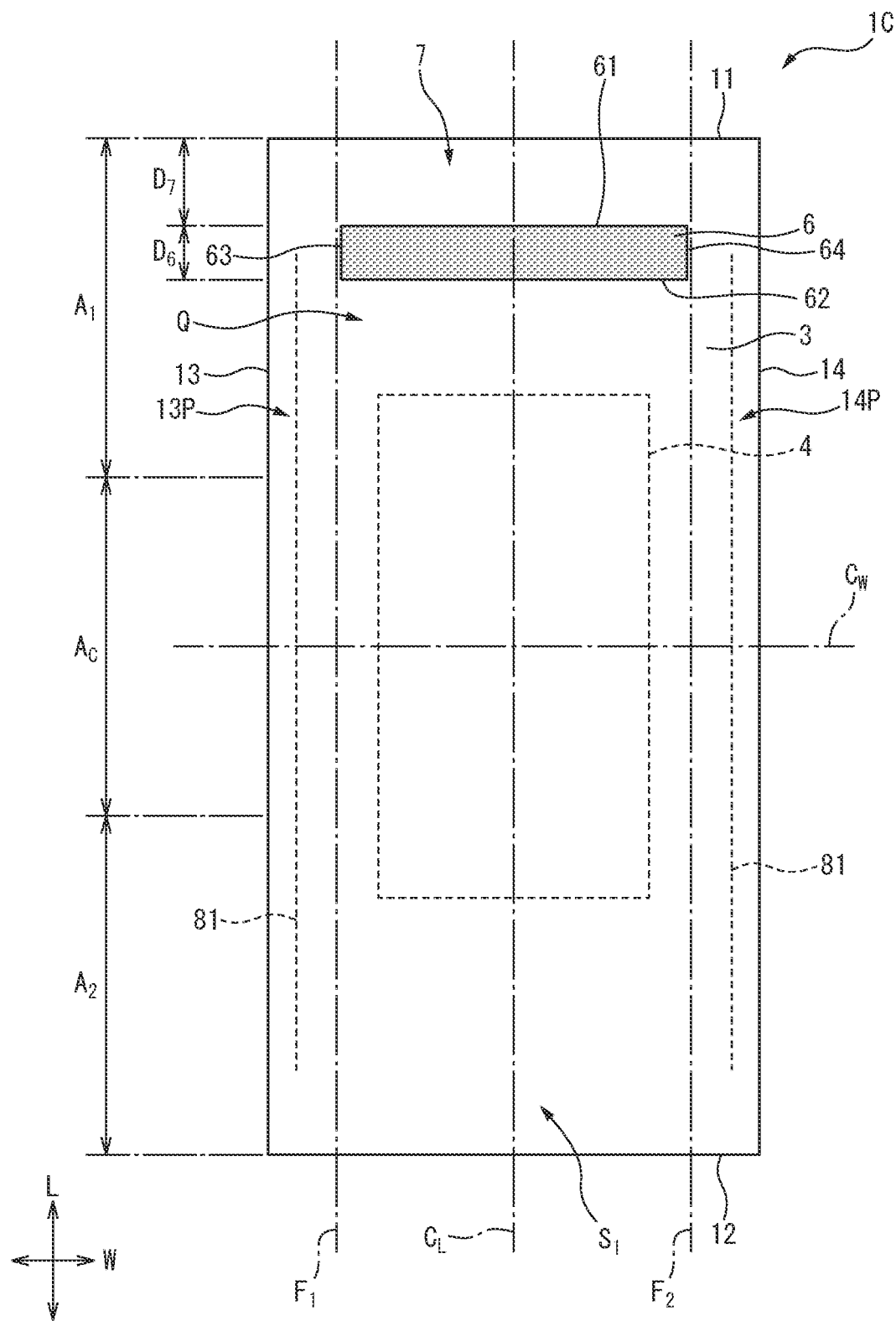
FIG. 10 is a plan view of the diaper for pets 1C according to one or more embodiments in an expanded state viewed from the first surface side in the thickness direction T.
Figure 11:
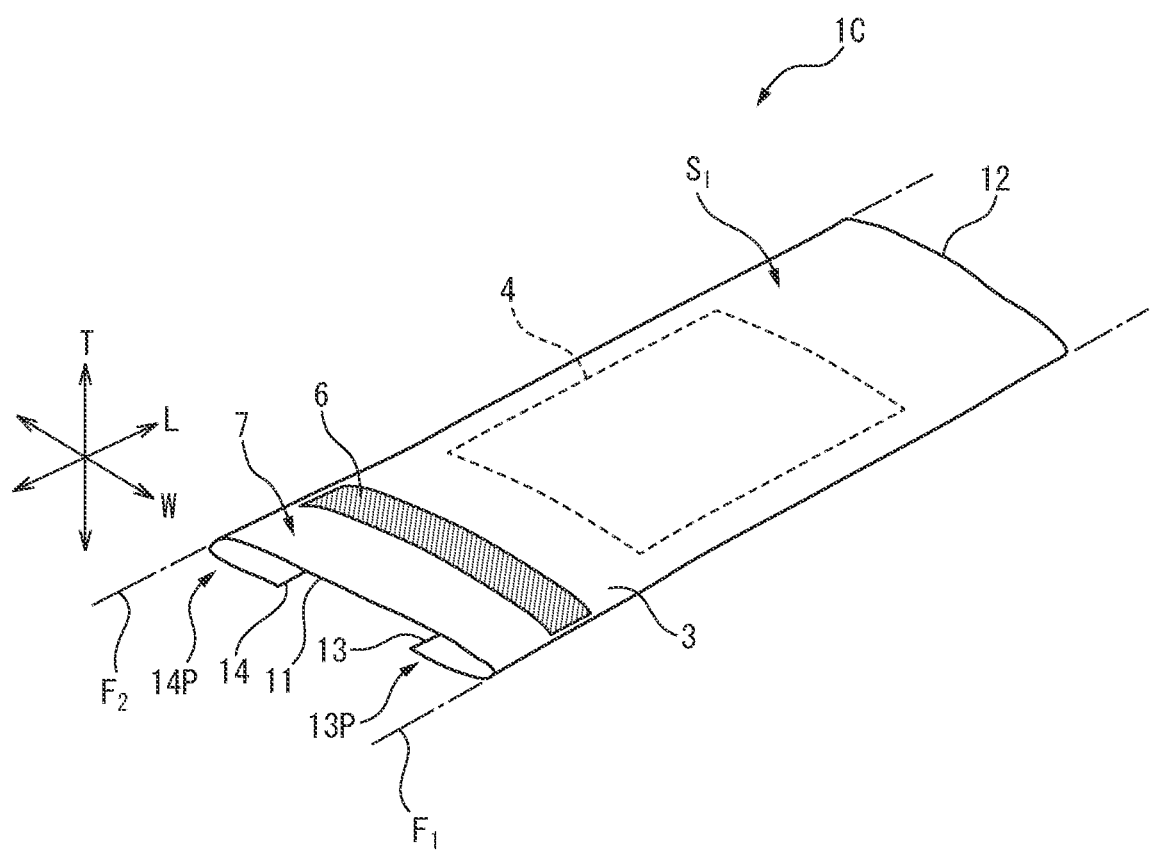
FIG. 11 is a perspective view which shows the state in which the one side end portion 13P and the other side end portion 14P in the width direction W of the diaper for pets 1C are folded toward the second surface side at two bending lines $F_1$, $F_2$ according to one or more embodiments.

FIG. 10 is a plan view of the diaper for pets 1C according to one or more embodiments in an expanded state viewed from the first surface side $D_1$ in the thickness direction T, and FIG. 11 is a perspective view which shows the state in which the one side end portion 13P and the other side end portion 14P in the width direction W of the diaper for pets 1C are folded toward the second surface side $D_2$ at two bending lines $F_1$, $F_2$.

The diaper for pets 1C according to one or more embodiments, as shown in FIG. 10, in a plan view, includes the two bending lines $F_1$, $F_2$ which extend in the longitudinal direction L at positions on the outer side in the width direction W with respect to the one side edge 63 and the other side edge 64 in the width direction W of the engagement portion 6, and in such a diaper for pets 1C, as shown in FIG. 11, each of the one side end portion 13P and the other side end portion 14P in the width direction W of the diaper for pets 1C is folded toward the second surface side $D_2$ at each of the bending lines $F_1$, $F_2$.

Incidentally, in one or more embodiments, the above described two bending lines may be disposed at positions which pass one side edge and the other side edge in the width direction of the engagement portion, as long as the both end portions in the width direction of the absorbent article for animals can be folded toward the second surface side.

In this manner, each of one side end portion and the other side end portion in the width direction of the absorbent article for animals is folded toward a second surface side at the two bending lines which are positioned at the above described specific positions, in addition to being able to make it difficult for the flap portion to be bent toward the first surface side, even when the flap portion is bent toward the first surface side so as to be adhered to the engagement portion, the flap portion can be easily torn off from the engagement portion only by spreading the one side end portion and the other side end portion in the width direction of the above described absorbent article which is folded toward the above described second surface side, or by pulling the one side end portion and the other side end portion toward the outer side in the width direction, whereby the tearing means of the flap portion other than the surplus portion which functions as the above described grasping portion can be secured, and the flap portion can be easily torn off from the engagement portion in a more reliable manner.

Further, when the absorbent article for animals is folded in this manner, there is also an advantage that it can be easily packaged with other plurality of absorbent articles for animals, in this folded state as it is, or in a state of being further folded in the longitudinal direction with the longitudinal direction central axis line $C_W$ which extends in the width direction, etc., as the folding axis.

Next, the diaper for pets 1D according to one or more embodiments is explained with reference to the drawings.

Figure 12:
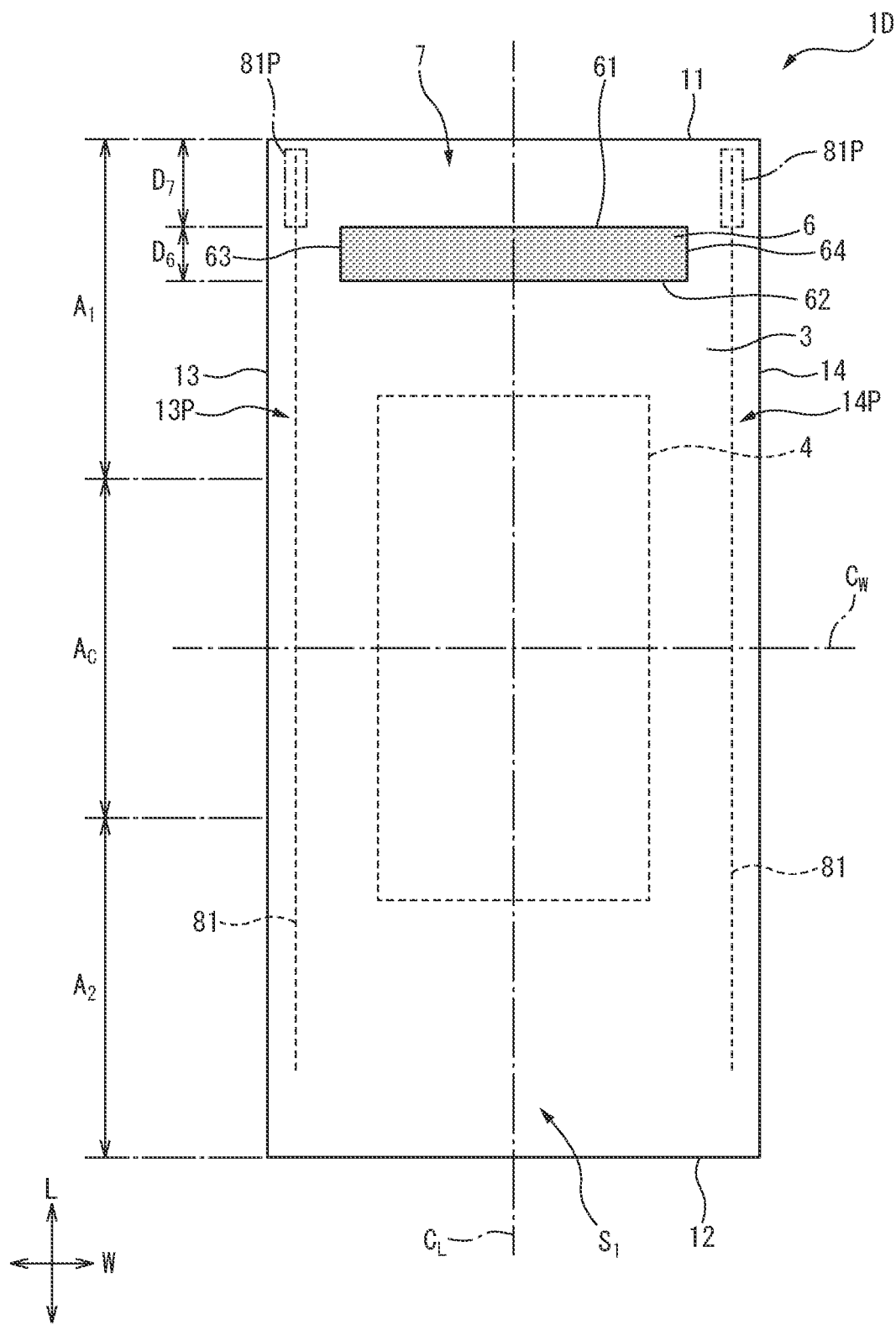
FIG. 12 is a plan view of the diaper for pets 1D according to one or more embodiments in an expanded state viewed from the first surface side in the thickness direction T.

FIG. 12 is a plan view of the diaper for pets 1D according to one or more embodiments in an expanded state viewed from the first surface side $D_1$ in the thickness direction T.

In the diaper for pets 1D according to one or more embodiments, as shown in FIG. 12, in a plan view, the pair of elastic members for side portion gather formation 81, 81 which extend in the longitudinal direction L (which are one example of "the elastic member" in the present invention) which are disposed at the one side end portion 13P and the other side end portion 14P in the width direction W, respectively, are both formed to be longer in the longitudinal direction L than those in the above described embodiments, and such pair of elastic members for side portion gather formation 81, 81 include, in a plan view, the overlapping portions 81P, 81P which overlap with the flap portion 7, respectively.

In this manner, when the pair of elastic members for side portion gather formation 81, 81 which are disposed at each of the one side end portion 13P and the other side end portion 14P in the width direction W of the diaper for pets 1D are disposed, in a plan view, so as to overlap with the flap portion 7, even when the flap portion 7 is bent toward the first surface side $D_1$ so as to be adhered to the engagement portion 6, the flap portion 7 can be torn off from the engagement portion 6 with less force by the stretching and shrinking action of the pair of elastic members for side portion gather formation 81, 81 in the flap portion 7.

Incidentally, in one or more embodiments, the longitudinal direction length of the pair of elastic members for side portion gather formation which are disposed at each of the one side end portion and the other side end portion in the width direction of the absorbent article for animals (that is, the elastic members which extend in the longitudinal direction) is not particularly limited. In one or more embodiments, an arbitrary longitudinal direction length, taking the close contact with the torso of an animal and the leakage prevention into consideration, may be adopted.

Next, the diaper for pets 1E according to one or more embodiments is explained with reference to the drawings.

Figure 13:
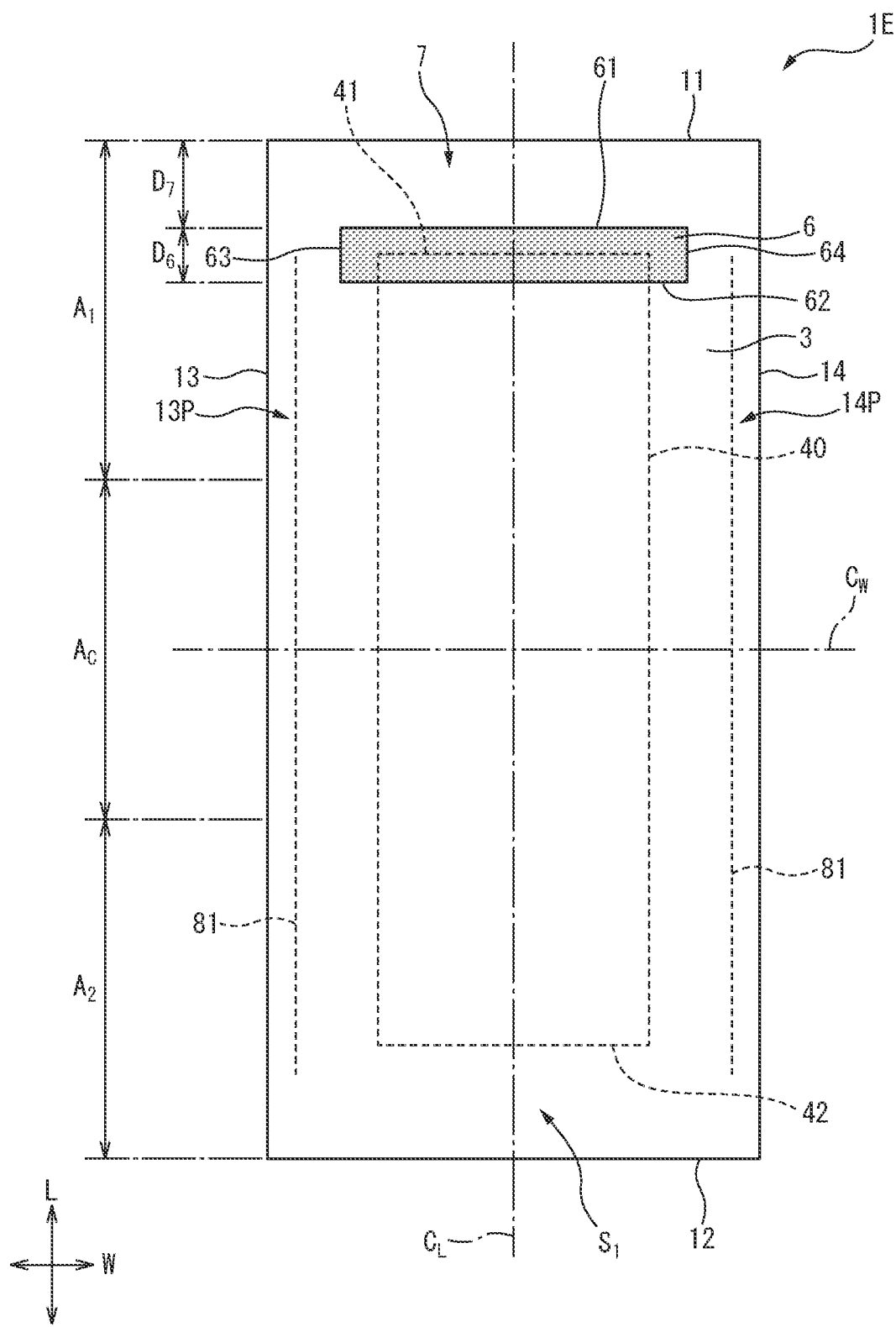
FIG. 13 is a plan view of the diaper for pets 1E according to one or more embodiments in an expanded state viewed from the first surface side in the thickness direction T.

FIG. 13 is a plan view of the diaper for pets 1E according to one or more embodiments in an expanded state viewed from the first surface side $D_1$ in the thickness direction T.

The diaper for pets 1E according to one or more embodiments includes, as shown in FIG. 13, the absorbent body 40 which is disposed between the top sheet 2 and the back sheet 3 (to be more specific, between the top sheet 2 and the back film 31), and in a plan view, which extends across from the first region $A_1$ to the second region $A_2$, and the absorbent body 40 is formed so that the longitudinal direction length (that is, the distance in the longitudinal direction L between the one side edge 41 and the other side edge 42 in the longitudinal direction L) is longer than that in the above described embodiments, and the one side edge 41 in the longitudinal direction L is disposed so as to overlap with the above described engagement portion 6 in the thickness direction T.

In this manner, when the one side edge 41 in the longitudinal direction L of the absorbent body 40 overlaps with the engagement portion 6 in the thickness direction T, the portion with high rigidity can be continuously secured from the engagement portion 6 toward the inner side in the longitudinal direction L by the existence of the absorbent body 40, whereby even when the flap portion 7 which has a relatively lower rigidity is bent toward the first surface side $D_1$ so as to be adhered to the engagement portion 6, the flap portion 7 can be more easily torn off from the engagement portion 6.

Incidentally, in one or more embodiments, it is not required for all of the one side edge 41 in the longitudinal direction L of the absorbent body 40 to overlap with the engagement portion 6 in the thickness direction T, and in accordance with the outer shape, etc., of the absorbent body 40 and the engagement portion 6, at least a portion of the one side edge 41 in the longitudinal direction L of the absorbent body 40 only needs to overlap with the engagement portion 6 in the thickness direction T.

Further, in one or more embodiments, the longitudinal direction length of the absorbent body is not particularly limited. In one or more embodiments, an arbitrary longitudinal direction length in accordance with the type, the body shape, the size, etc., of the attaching target animal may be adopted.

The characteristics of each of the above described embodiments may be suitably combined, substituted, or modified, etc.

Further, the absorbent article for animals according to one or more embodiments of the present invention may include an arbitrary configurational member or configurational element known in the art, other than the above described various configurational members. For example, the absorbent article for animals according to one or more embodiments may include, between the nonwoven fabric which forms the first surface and the nonwoven fabric which forms the second surface, a diffusion sheet which is capable of letting the liquid excrements such as urine, etc., diffuse in the longitudinal direction and/or the width direction.

Further, the absorbent article for animals according to one or more embodiments may include, at an engagement portion peripheral region which in a plan view, is the peripheral region of the engagement portion in the flap portion and the longitudinal direction distance from the engagement portion is or less than the longitudinal direction length of the engagement portion, one or a plurality of compressed portions which are depressed from the first surface of the absorbent article in the thickness direction.

Figure 24A:
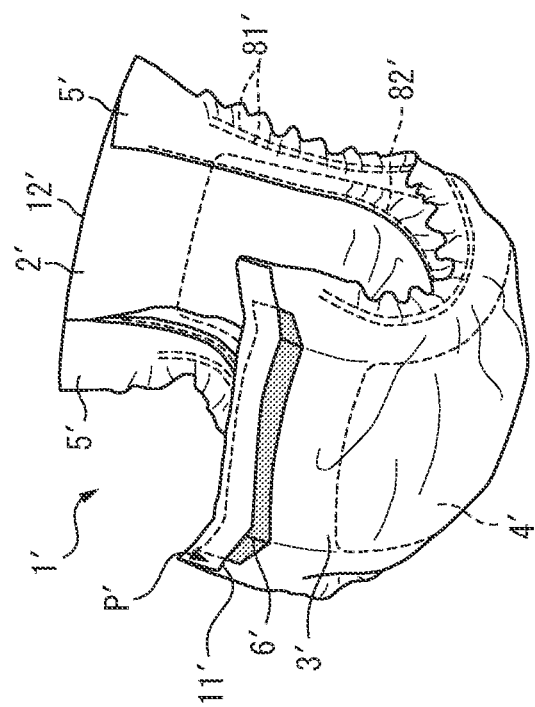
FIG. 24A and FIG. 24B are perspective views which show how the flap portion V of the conventional diaper for pets 1' is bent toward the back surface layer side so as to be adhered to the engagement portion 6' according to one or more embodiments.

When the absorbent article for animals includes such one or a plurality of compressed portions in the engagement portion peripheral region of the flap portion, since it is difficult for the engagement portion peripheral region to be bent by the compressed portion with high rigidity, not only the possibility of the above described flap portion being adhered to the engagement portion can be even more decreased (that is, it is difficult for the event itself as shown in FIG. 24(a) in the conventional absorbent article for animals to be caused), but also, even if the flap portion is bent toward the first surface side and is adhered to the engagement portion, since the surface on the first surface side of the compressed portion in the above described engagement portion peripheral region is formed to be a surface with high fiber density and smoothness due to the configurational fibers of the nonwoven fabric which forms the first surface being compacted, when tearing off the flap portion from the engagement portion by grasping the above described surplus portion, the flap portion can be easily torn off with less force.

Further, when the flap portion is torn off from the engagement portion, it is difficult for the configurational fibers of the nonwoven fabric which forms the adhered surface (the first surface) of the flap portion to come off (that is, it is difficult for the configurational fibers of the nonwoven fabric which forms the first surface of the flap portion to remain in the engagement portion after tearing off the flap portion), whereby there is also an advantage that it is difficult for the engagement force of the engagement portion after the flap portion is torn off to be decreased.

Incidentally, the above described "longitudinal direction distance from the engagement portion" means the longitudinal direction length taking the one side edge (the outer side edge) in the longitudinal direction of the engagement portion as the starting point to the target position on the outer side in the longitudinal direction, and the above described "engagement portion peripheral region" means the region in which the longitudinal direction distance from the engagement portion is or less than the longitudinal direction length of the engagement portion (that is, the region which extends from the one side edge in the longitudinal direction of the engagement portion toward the outer side in the longitudinal direction, and up to the portion in which the longitudinal direction distance from the one side edge in the longitudinal direction of the engagement portion is to be equal to the longitudinal direction length of the engagement portion).

In a case in which the above described compressed portions are provided in the engagement portion peripheral region of the flap portion, the outer shape and the disposing manner of the compressed portions are not particularly. For example, in one or more embodiments, the compressed portions, in a plan view, may be formed in an arbitrary outer shape such as a substantially circular shape; an oval shape, a triangular shape; a rectangular shape such as a square, a diamond shape, etc.; a cross shape; one or a plurality of linear shapes (for example, continuous or non-continuous straight line, wavy line, zigzag line, etc.); one or a plurality of belt-like shapes; design drawings of various symbols, patterns, animals and plants, various characters, etc., or in an arbitrary form such as staggered-like, grid, stripe, and random, etc.

Incidentally, the above described compressed portions may be formed in the region other than the engagement portion peripheral region of the flap portion (for example, any region from the above described first region to the second region, or in all of the regions, etc.).

Further, the number of the compressed portions and the size of each of the compressed portions, etc., are not particularly limited. In one or more embodiments, the compressed portion can be formed with one or more numbers and with an arbitrary size.

Still further, in a case in which the above described compressed portions are provided in the engagement portion peripheral region of the flap portion, the compressed portions are preferably disposed at the region which has the width direction length that is longer than the width direction length of the engagement portion and/or the region which has the longitudinal direction length that is longer than the longitudinal direction length of the engagement portion. When the compressed portions are disposed in this manner, not only it is difficult for the wider range of region in the flap portion to be bent by the rigidity of the above described compressed portion, but also even when the flap portion is bent toward the first surface side so as to be in contact with the engagement portion, the possibility of the bent flap portion of being adhered to the engagement portion can be more reliably decreased.

The forming means of the above described compressed portion is not particularly limited, and an arbitrary embossing means known in the art may be adopted. For example, the nonwoven fabric to form the first surface (that is, the back sheet or the top sheet) alone, or laminated layers which include at least the nonwoven fabric to form the first surface and the back film are compressed from the first surface side of the nonwoven fabric to form the first surface in the thickness direction by using heated or unheated embossing means for compressed portion formation including one or a plurality of protruded portions, whereby the above described compressed portions can be formed.

Further, in a case in which the absorbent article for animals includes the joining portion which joins the back film and the back sheet, the joining portion preferably includes the non-overlapping portion which does not overlap with the above described compressed portions in a plan view. When the joining portion includes such a non-overlapping portion, the non-overlapping portion can make it difficult for the back sheet between the adjacent compressed portions to be lifted up, whereby even when the above described flap portion is bent toward the first surface side and comes close to the engagement portion, since it is difficult not only for the above described compressed portions but also for the non-overlapping portion to be in contact with the engagement portion, the possibility of the flap portion on which the compressed portions are formed being adhered to the engagement portion can be more reliably decreased.

The method of manufacturing the absorbent article for animals by using the above described various configurational members is not particularly limited, and an arbitrary manufacturing method known in the art can be adopted. For example, the diaper for pets 1 according to one or more embodiments can be manufactured by overlapping various members which configure the diaper for pets 1, that is, by overlapping the pair of side sheets 5, 5 on which the pair of elastic members for three-dimensional gather formation 82, 82 are arranged at the end portions on the inner side in the width direction W, the top sheet 2, the absorbent body 4, the back film 31, the pair of elastic members for side portion gather formation 81, 81, the back sheet 3 and the engagement portion 6, in the disposing manner as shown in FIG. 2 to FIG. 5, and by joining the same by an arbitrary joining means (for example, a bonding method by using a hot melt adhesive agent, a heat sealing method, and an ultrasonic bonding method, etc.).

Hereinbelow, embodiments of the present invention are explained in detail with reference to the drawings.

Figure 14:
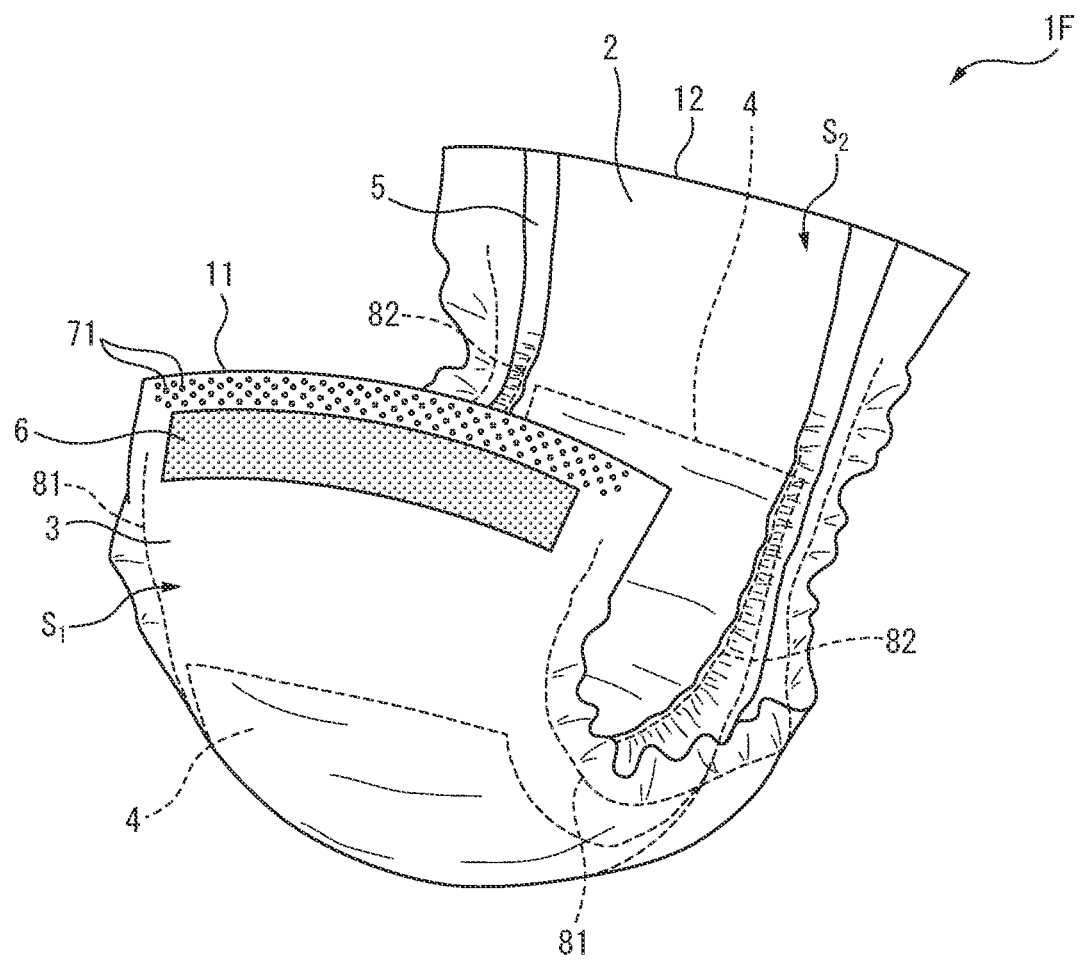
FIG. 14 is a perspective view of the diaper for pets 1F according to one or more embodiments.
Figure 15:
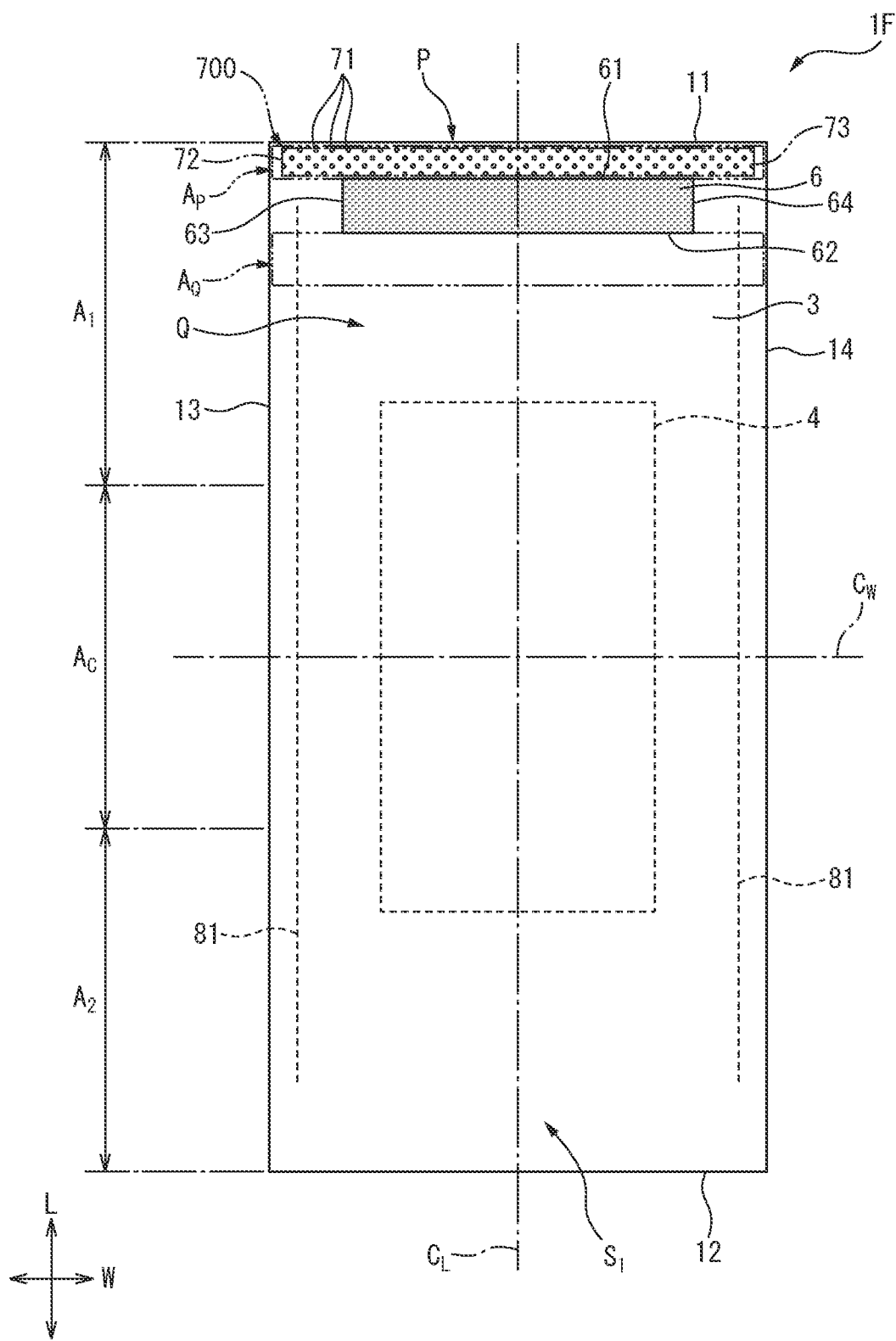
FIG. 15 is a plan view of the diaper for pets 1F in an expanded state viewed from the first surface side (the back sheet side) in the thickness direction T according to one or more embodiments.
Figure 17:
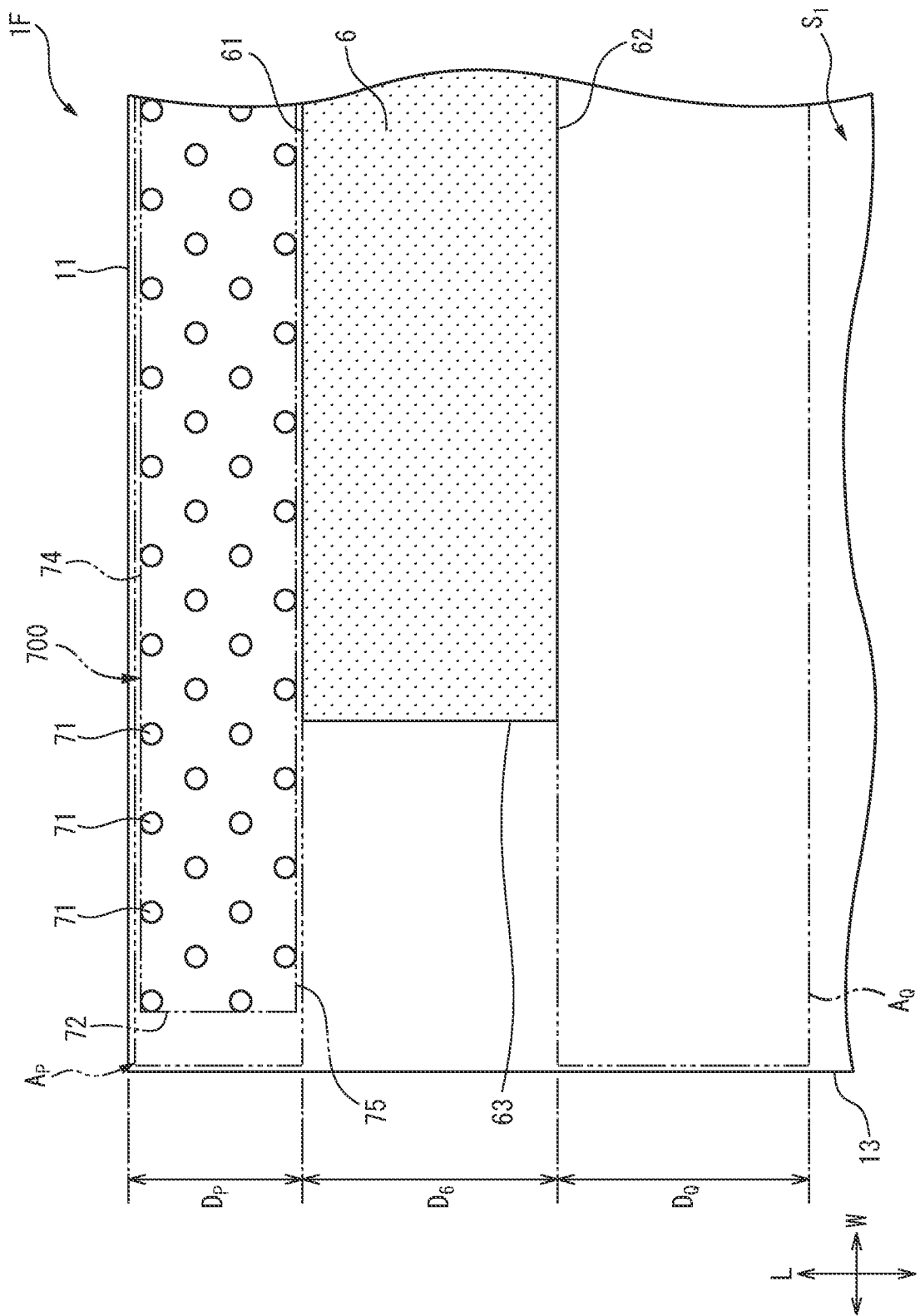
FIG. 17 is a principal portion enlarged plan view of the diaper for pets 1F in an expanded state viewed from the first surface side in the thickness direction T according to one or more embodiments.

FIG. 14 is a perspective view of the diaper for pets 1F according to tone or more embodiments, FIG. 15 is a plan view of the diaper for pets 1F in an expanded state viewed from the first surface side (the back sheet side) in the thickness direction T, FIG. 16 is an end view of the longitudinal direction cross section along the width direction central axis line $C_L$ which extends in the longitudinal direction L of the diaper for pets 1F. Further, FIG. 17 is a principal portion enlarged plan view of the diaper for pets 1F in an expanded state viewed from the first surface side in the thickness direction T.

The diaper for pets 1F according to one or more embodiments includes, as shown in FIG. 14, FIG. 15, FIG. 16 and FIG. 17, in a plan view, the compressed portion formation region 700 which is positioned on the outer side in the longitudinal direction L with respect to the above described engagement portion 6 (that is, in the flap portion P), overlaps with the engagement portion peripheral region $A_P$ which is positioned on the outer side in the longitudinal direction L and in which the longitudinal direction distance $D_P$ from the engagement portion 6 is or less than the longitudinal direction length $D_6$ of the engagement portion 6, and includes the plurality of compressed portions 71 which are depressed from the first surface $S_1$ of the diaper for pets 1F in the thickness direction T, and further, the above described first region $A_1$ has the compressed portion area ratio which is greater than the compressed portion area ratio in the second region $A_2$. Incidentally, in the diaper for pets 1F according to one or more embodiments, since the compressed portions are not formed in the second region $A_2$, the compressed portion area ratio in the second region $A_2$ is 0%.

Figure 24C:
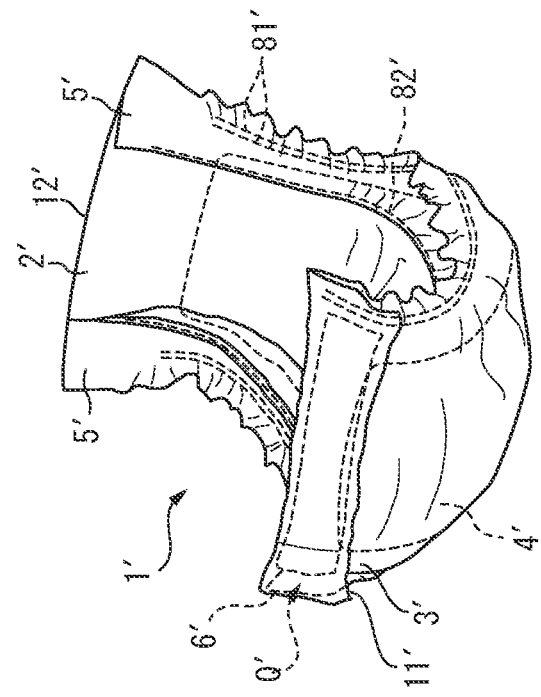
FIG. 24C is a perspective view which shows how the inner side portion Q' in the longitudinal direction L with respect to the engagement portion 6' of the conventional diaper for pets 1' is bent toward the back surface layer side so as to be adhered to the engagement portion 6' according to one or more embodiments.
Figure 24B:
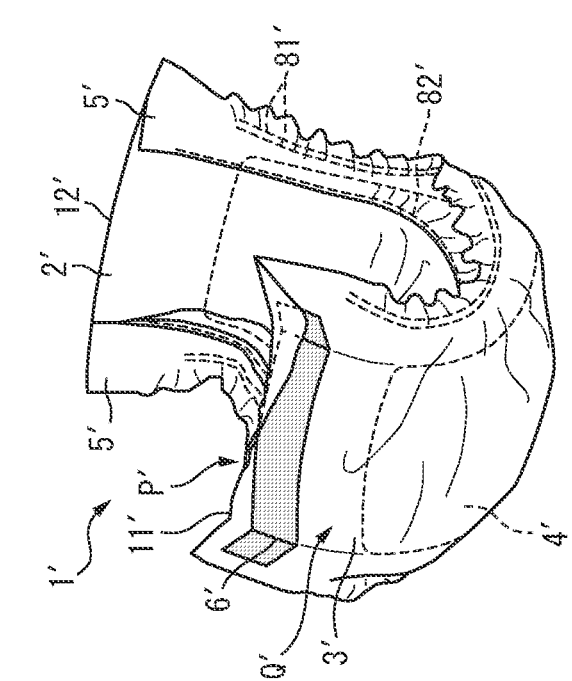

In this manner, since the diaper for pets 1F according to one or more embodiments includes the plurality of compressed portions 71 in the engagement portion peripheral region $A_P$ of the first region $A_1$, and it is difficult for the engagement portion peripheral region $A_P$ to be bent by the compressed portions 71 with high rigidity, it is difficult for the above described flap portion P to be adhered to the engagement portion 6 (that is, it is difficult for the event as shown in FIG. 24(b) in the conventional absorbent article for animals to be caused), and as a result, it is difficult for the engagement force of the engagement portion 6 to be decreased.

Further, even if the above described engagement portion peripheral region $A_P$ is bent toward the first surface side $D_1$ and the flap portion P is adhered to the engagement portion 6, since the surface of the first surface side $D_1$ of the compressed portions 71 is formed to be a surface with high fiber density and smoothness due to the configurational fibers of the nonwoven fabric (the back sheet 3) which forms the first surface $S_1$ being compacted, it is easy for the flap portion P which has been adhered to the engagement portion 6 to be torn off from the engagement portion 6, and further, also when the flap portion P is torn off from the engagement portion 6, it is difficult for the configurational fibers of the nonwoven fabric which forms the adhered surface (that is, the first surface $S_1$) of the flap portion P to come off (that is, it is difficult for the configurational fibers of the nonwoven fabric which forms the first surface $S_1$ of the flap portion P to remain in the engagement portion 6 after tearing off the flap portion P), and as a result, it is difficult for the engagement force of the engagement portion 6 to be decreased.

Still further, in the diaper for pets 1F according to one or more embodiments, the compressed portion area ratio in the first region $A_1$ is configured to be greater than the compressed portion area ratio in the second region $A_2$, and since the second region $A_2$ has a relatively lower rigidity and is soft, the second region $A_2$ can engage with the engagement portion 6 in the above described first region $A_1$ with high joining strength while following the shape of the torso of an animal, such as a dog, etc.

As described above, by the diaper for pets 1F according to one or more embodiments, it is difficult for the engagement force of the engagement portion 6 to be decreased and it is difficult to come off from the torso of the attached animal.

Incidentally, in the absorbent article for animals according to one or more embodiments, the disposed position of the compressed portion formation region and the shape, etc., of the compressed portions are not limited to the above described embodiments, and as in embodiments which will be described later, the compressed portion formation region 700 may be positioned in the portion Q on the inner side in the longitudinal direction L with respect to the above described engagement portion 6, and at the position which overlaps with the engagement portion peripheral region $A_Q$ on the inner side in the longitudinal direction L in which the longitudinal direction distance $D_Q$ from the engagement portion 6 is or less than the longitudinal direction length $D_6$ of the engagement portion 6, and further, one or more compressed portions need only to be formed within the compressed portion formation region.

When the above described compressed portion formation region 700 is disposed at the position which overlaps with the engagement portion peripheral region $A_Q$ of the portion Q on the inner side in the above described longitudinal direction L, since it is difficult for the engagement portion peripheral region $A_Q$ to be bent by the compressed portions 71 with high rigidity, it is difficult for the portion Q on the inner side in the above described longitudinal direction L to be adhered to the engagement portion 6 (that is, it is difficult for the event as shown in FIG. 24(c) in the conventional absorbent article for animals to be caused), and as a result, it is difficult for the engagement force of the engagement portion 6 to be decreased.

Further, even if the above described engagement portion peripheral region $A_Q$ is bent toward the first surface side $D_1$ and the above described portion Q on the inner side is adhered to the engagement portion 6, since the surface of the first surface side $D_1$ of the compressed portions 71 is formed, as described above, to be a surface with high fiber density and smoothness due to the configurational fibers of the nonwoven fabric which forms the first surface $S_1$ being compacted, it is easy for the portion Q on the inner side in the above described longitudinal direction L which has been adhered to the engagement portion 6 to be torn off from the engagement portion 6, and further, also when the portion Q is torn off from the engagement portion 6, it is difficult for the configurational fibers of the nonwoven fabric which forms the adhered surface (that is, the first surface $S_1$) of the portion Q to come off (that is, it is difficult for the configurational fibers of the nonwoven fabric which forms the first surface $S_1$ of the above described portion Q on the inner side to remain in the engagement portion 6 after tearing off the above described portion Q on the inner side), and as a result, it is difficult for the engagement force of the engagement portion 6 to be decreased.

[Compressed Portion Formation Region]

In the above described diaper for pets 1F according to one or more embodiments, the compressed portion formation region 700 is disposed, as shown in FIG. 14, FIG. 15, FIG. 16 and FIG. 17, in a plan view, at the position on the outer side in the longitudinal direction L with respect to the above described engagement portion 6 (that is, in the flap portion P), overlaps with the engagement portion peripheral region $A_P$ in which the longitudinal direction distance $D_P$ from the engagement portion 6 is or less than the longitudinal direction length $D_6$ of the engagement portion 6, and includes the plurality of compressed portions 71 which are depressed from the first surface $S_1$ of the diaper for pets 1F in the thickness direction T.

Incidentally, the above described "longitudinal direction distance from the engagement portion" means the longitudinal direction length taking the one side edge (the outer side edge) in the longitudinal direction of the engagement portion as the starting point to the target position on the outer side in the longitudinal direction, or the longitudinal direction length taking the other side edge (the inner side edge) in the longitudinal direction of the engagement portion as the starting point to the target position on the inner side in the longitudinal direction.

Further, the above described "engagement portion peripheral region" means the region in which the longitudinal direction distance from the engagement portion is or less than the longitudinal direction length of the engagement portion, and includes not only the region which extends from the one side edge (the outer side edge) in the longitudinal direction of the engagement portion to the outer side in the longitudinal direction and the longitudinal direction distance from the engagement portion is or less than the longitudinal direction length of the engagement portion (which is the region that corresponds to the engagement portion peripheral region $A_P$ in FIG. 15 and FIG. 17), and the region which extends from the other side edge (the inner side edge) in the longitudinal direction of the engagement portion to the inner side in the longitudinal direction and the longitudinal direction distance from the engagement portion is or less than the longitudinal direction length of the engagement portion (which is the region that corresponds to the engagement portion peripheral region $A_Q$ in FIG. 15 and FIG. 17), but also the outer side in the width direction of the one side edge and the other side edge in the width direction of the engagement portion.

For example, in a case in which the longitudinal direction length between the one side edge in the longitudinal direction of the absorbent article for animals and the one side edge in the longitudinal direction of the engagement portion is or more than the longitudinal direction length of the engagement portion (that is, in a case in which the longitudinal direction length of the flap portion is or more than the longitudinal direction length of the engagement portion), the engagement portion peripheral region which is positioned on the outer side in the longitudinal direction of the engagement portion is the region which extends from the one side edge in the longitudinal direction of the engagement portion to the outer side in the longitudinal direction and up to the portion in which the longitudinal direction distance from the one side edge in the longitudinal direction of the engagement portion is to be equal to the longitudinal direction length of the engagement portion, and in a case in which the longitudinal direction length between the one side edge in the longitudinal direction of the absorbent article for animals and the one side edge in the longitudinal direction of the engagement portion is less than the longitudinal direction length of the engagement portion (that is, in a case in which the longitudinal direction length of the flap portion is less than the longitudinal direction length of the engagement portion), the engagement portion peripheral region which is positioned on the outer side in the longitudinal direction of the engagement portion is the region which extends from the one side edge in the longitudinal direction of the engagement portion to the outer side in the longitudinal direction and up to the one side edge in the longitudinal direction of the absorbent article for animals.

Incidentally, in the absorbent article for animals according to one or more embodiments, as described above, the disposed position of the compressed portion formation region is not limited to the above describe embodiments, and as in the embodiments which will be described later, the compressed portion formation region 700 may be positioned in the portion Q on the inner side in the longitudinal direction L with respect to the engagement portion 6, and at the position which overlaps with the engagement portion peripheral region $A_Q$ on the inner side in the longitudinal direction L in which the longitudinal direction distance $D_Q$ from the engagement portion 6 is or less than the longitudinal direction length $D_6$ of the engagement portion 6.

The absorbent article for animals according to one or more embodiments includes, as described above, one or a plurality of compressed portions in the engagement portion peripheral region of the first region, whereby it is difficult for the engagement portion peripheral region to be bent by the compressed portions with high rigidity, and thus it is difficult for the above described flap portion, etc. to be adhered to the engagement portion (that is, it is difficult for the event as shown in FIG. 24(b) and FIG. 24(c) in the conventional absorbent article for animals to be caused), and as a result, it is difficult for the engagement force of the engagement portion to be decreased.

Incidentally, in the present description, "the compressed portion formation region" means, in a plan view, the region which is surrounded by four virtual straight lines of the virtual straight line which passes the edge on the outer side in the longitudinal direction of the compressed portion positioned on the most outer side in the longitudinal direction and extends in the width direction; the virtual straight line which passes the edge on the inner side in the longitudinal direction of the compressed portion positioned on the most inner side in the longitudinal direction and extends in the width direction; the virtual straight line which passes the edge on the outer side in the width direction of the compressed portion positioned on the most outer side on one side in the width direction and extends in the longitudinal direction; and the virtual straight line which passes the edge on the outer side in the width direction of the compressed portion positioned on the most outer side on the other side in the width direction and extends in the longitudinal direction, and in the above described embodiments, the compressed portion formation region 700 is, as shown in FIG. 15 and FIG. 17, in a plan view, the region which is surrounded by four edges of: the one side edge 74 in the longitudinal direction L positioned on the outer side in the longitudinal direction L; the other side edge 75 in the longitudinal direction L positioned on the inner side in the longitudinal direction L; the one side edge 72 in the width direction W positioned on the one side in the width direction W; and the other side edge 73 in the width direction W positioned on the other side in the width direction W, which overlap with the above described four virtual straight lines.

Further, in one or more embodiments, each of the plurality of compressed portions 71 within the compressed portion formation region 700 is, as shown in FIG. 16, formed so as to be depressed from the first surface $S_1$ of the diaper for pets 1F in the thickness direction T, and further, the surface on the first surface side $D_1$ of the compressed portions 71 is formed to be a surface with high fiber density and smoothness due to the configurational fibers of the nonwoven fabric (the back sheet 3) which forms the first surface $S_1$ of the diaper for pets 1F being compacted.

When the compressed portions 71 are formed in this manner, even if the above described flap portion P is bent so as to be in contact with the engagement portion 6, not only the contact area of the first surface $S_1$ of the flap portion P and the engagement portion 6 can be decreased by the compressed portions 71 which are depressed from the first surface $S_1$ in the thickness direction T, but also it is difficult for the hook portions 6f of the engagement portion 6 to be engaged to the surface on the first surface side $D_1$ of the compressed portions 71, whereby it is difficult for the first surface $S_1$ of the flap portion P to be adhered to the engagement portion 6, and further, even when the first surface $S_1$ of the above described flap portion P has been adhered to the engagement portion 6, the surface form of the first surface side $D_1$ of the above described compressed portions 71 can decrease the joining strength of the engagement of the configurational fibers on the surface on the first surface side $D_1$ of the compressed portions 71 and the hook portions 6f of the engagement portion 6, whereby it is easier for the flap portion P which has been adhered to the engagement portion 6 to be torn off from the engagement portion 6, and also, when the flap portion P is torn off from the engagement portion 6, it is difficult for the configurational fibers of the nonwoven fabric which forms the adhered surface (the first surface $S_1$) of the flap portion P to come off (that is, it is difficult for the configurational fibers of the nonwoven fabric which forms the first surface $S_1$ of the flap portion P to remain in the engagement portion 6 after tearing off the flap portion P).

In one or more embodiments, each of the plurality of compressed portions 71 has, as shown in FIG. 15 and FIG. 17, in a plan view, a substantially circular dot-like outer shape, and is disposed in a staggered form. When the plurality of compressed portions 71 are disposed in such a staggered form, in the compressed portion formation region 700, not only the compressed portions 71 which are difficult to be engaged with the engagement portion 6 can be disposed evenly overall, but also the uneven localization of rigidity is less likely to be caused, whereby the effect of embodiments of the present invention can be exhibited more advantageously.

Incidentally, in one or more embodiments, the outer shape and the disposing manner of each of the compressed portions are not particularly limited. For example, in one or more embodiments, the compressed portions, in a plan view, may be formed in an arbitrary outer shape such as an oval shape, a triangular shape; a rectangular shape such as a square, a diamond shape, etc.; a cross shape; one or a plurality of linear shapes (for example, continuous or non-continuous straight line, wavy line, zigzag line, etc.); one or a plurality of belt-like shapes; design drawings of various symbols, patterns, animals and plants, various characters, etc., and can be disposed in an arbitrary form such as grid, stripe, and random, etc.

Further, in one or more embodiments, the number of the compressed portions and the size of each of the compressed portions, etc., are not particularly limited. In one or more embodiments, the compressed portion can be formed with one or more numbers and with an arbitrary size, however, as described above, it is required that the compressed portion area ratio of the first region is formed so as to be greater than the compressed portion area ratio of the second region.

Incidentally, in one or more embodiments, since the compressed portions are not formed in the second region $A_2$ of the diaper for pets 1F, the compressed portion area ratio in the second region $A_2$ is 0%, however, embodiments of the present invention are not limited to such an aspect, and the absorbent article for animals may include the compressed portions in the second region and the center region, other than the first region, as long as the compressed portion area ratio in the first region is greater than the compressed portion area ratio in the second region.

Note that, in the present description, "the compressed portion area ratio" means the ratio (%) of the total plan view area of the compressed portions with respect to the plan view area of the target region (for example, the first region, second region, etc.), and for example, can be obtained by calculating the total plan view area of the compressed portions from the plan view area of each of the compressed portions and the number thereof by using an arbitrary magnifying means such as a magnifying glass or a microscope, etc., dividing the calculated total plan view area of the compressed portions by the plan view area of the target region which has been separately measured, and multiplying by 100.

Incidentally, the magnitude relationship of the compressed portion area ratios within each of the regions can be determined by visual observation, etc., in a case in which the magnitude relationship is clear by visual observation, etc., as in the above described embodiments, and in a case in which the magnitude relationship is difficult by visual observation, etc., the compressed portion area ratios in each of the regions may be calculated as described above so as to be compared, whereby the magnitude relationship can be determined.

In this manner, in the absorbent article for animals according to one or more embodiments, the compressed portion area ratio in the first region is configured to be greater than the compressed portion area ratio in the second region, and since the second region has a relatively lower rigidity and is soft, the second region can engage with the engagement portion in the above described first region with high joining strength while following the shape of the torso of an animal.

Further, in the diaper for pets 1F according to the above described embodiments, each of the one side edge 72 and the other side edge 73 in the width direction W of the compressed portion formation region 700 is positioned on the outer side in the width direction W with respect to the one side edge 63 and the other side edge 64 in the width direction W of the engagement portion 6, that is, the compressed portion formation region 700 has a longer width direction length than the width direction length of the engagement portion 6. In this manner, when the compressed portion formation region 700 has a longer width direction length than the width direction length of the engagement portion 6, it is difficult for a wider range of region in the width direction W in the flap portion P to be bent, and further, even when the flap portion P is bent (especially in a case in which the end portion in the width direction W of the diaper for pets 1F is also bent), the possibility of the bent flap portion P being adhered to the engagement portion 6 can be even more decreased. Accordingly, it is more difficult for the engagement force of the engagement portion 6 to be decreased and which is more difficult to come off from the torso of the attached animal.

Further, in the diaper for pets 1F according to the above described embodiments, the compressed portion formation region 700 extends, in the longitudinal direction L, from the one side edge 61 in the longitudinal direction L of the engagement portion 6 to the one side edge 11 in the longitudinal direction L of the diaper for pets 1F. In this manner, when the compressed portion formation region 700 extends, in the longitudinal direction L, from the one side edge 61 in the longitudinal direction L of the engagement portion 6 to the one side edge 11 in the longitudinal direction L of the diaper for pets 1F, that is, when the compressed portion formation region 700 extends across the whole flap portion P, the diaper for pets 1F can make it difficult for especially the flap portion P to be bent, and even if the flap portion P is bent, the possibility of the bent flap portion P being adhered to the engagement portion 6 can be more reliably decreased, regardless of how the flap portion P is bent.

In one or more embodiments, the disposing position and the disposing manner of the compressed portion formation region are not limited to those in the above described embodiments, and an arbitrary disposing position and disposing manner in accordance with the type, the body shape, the size, etc., of the attaching target animal may be adopted.

Hereinbelow, the disposing positions and disposing manners of the compressed portion formation region which may be adopted to the absorbent article for animals are explained in detail while exemplifying other embodiments which are different from the above described embodiments. Incidentally, in one or more embodiments, the configurations other than those different from the above described embodiments are basically the same as those in the above described embodiments, and thus the explanations thereof will be omitted.

Figure 18:
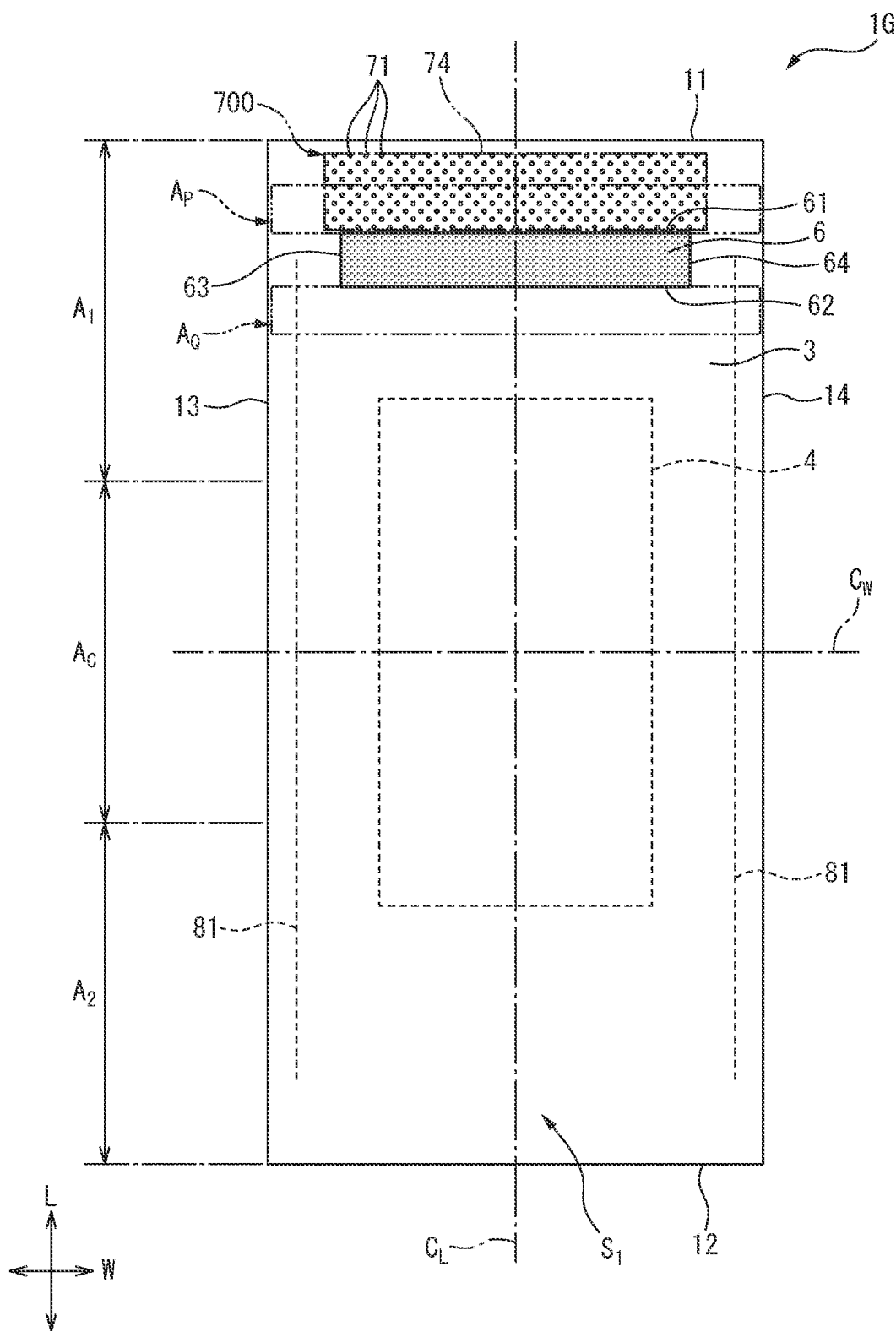
FIG. 18 is a plan view of the diaper for pets 1G according to one or more embodiments in an expanded state viewed from the first surface side in the thickness direction T.

FIG. 18 is a plan view of the diaper for pets 1G according to one or more embodiments in an expanded state viewed from the first surface side $D_1$ in the thickness direction T.

In the diaper for pets 1G according to one or more embodiments, as shown in FIG. 18, the length from the one side edge 61 in the longitudinal direction L of the engagement portion 6 to the one side edge 11 in the longitudinal direction L of the diaper for pets 1G (that is, the longitudinal direction length of the flap portion P) is formed to be longer than that in the diaper for pets 1F according to the above described embodiments, the compressed portion formation region 700 is disposed so as to overlap with the engagement portion peripheral region $A_P$ on the outer side in the longitudinal direction L, in which the longitudinal direction distance from the engagement portion 6 is or less than the longitudinal direction length of the engagement portion 6, and further, is disposed, in the longitudinal direction L, so as to extend from the one side edge 61 in the longitudinal direction L of the engagement portion 6 toward the outer side in the longitudinal direction L, and so as to have the longitudinal direction length which is longer than the longitudinal direction length of the engagement portion 6 (that is, the longitudinal direction length between the one side edge 61 and the other side edge 62 in the longitudinal direction L of the engagement portion 6).

When the compressed portion formation region 700 is disposed in this manner, even in a case in which the flap portion P is formed to be long in the longitudinal direction L as in one or more embodiments, not only the diaper for pets 1G can make it difficult for the portion which affects the adhesion of the flap portion P to the engagement portion 6 to be bent, but also even if the flap portion P is bent, the possibility of the bent flap portion P being adhered to the engagement portion 6 can be more reliably decreased.

Further, when the flap portion P has a longitudinal direction length which is longer than a longitudinal direction length of the engagement portion 6 as in one or more embodiments, when the flap portion P is adhered to the engagement portion 6, by regarding the portion longer than the longitudinal direction length of the engagement portion 6 in the flap portion P as the grasping portion, the flap portion P can be easily torn off by grasping the grasping portion, and the advantage of not taking much trouble in attaching the diaper for pets 1G to the torso of an animal can also be obtained.

Figure 19:
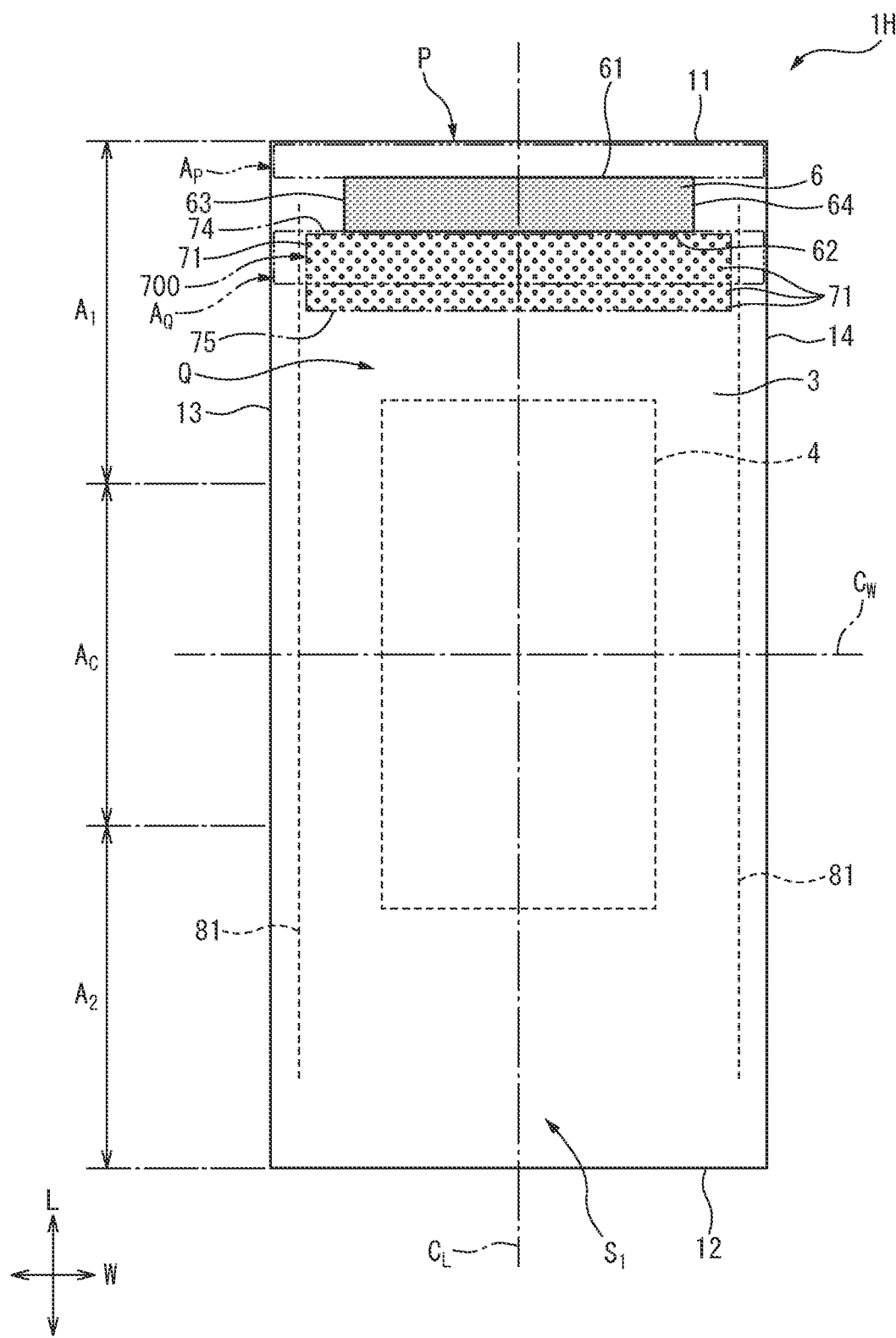
FIG. 19 is a plan view of the diaper for pets 1H according one or more embodiments in an expanded state viewed from the first surface side in the thickness direction T.

FIG. 19 is a plan view of the diaper for pets 1H according to one or more embodiments in an expanded state viewed from the first surface side $D_1$ in the thickness direction T.

In the diaper for pets 1H according to one or more embodiments, as shown in FIG. 19, the compressed portion formation region 700 is disposed in the portion Q on the inner side in the longitudinal direction L with respect to the engagement portion 6, and to be more specific, the compressed portion formation region 700 is disposed so as to overlap with the engagement portion peripheral region $A_Q$ on the inner side in the longitudinal direction L in which the longitudinal direction distance $D_Q$ from the engagement portion 6 is or less than the longitudinal direction length $D_6$ of the engagement portion 6, and further, is disposed, in the longitudinal direction L, so as to extend from the other side edge 62 in the longitudinal direction L of the engagement portion 6 toward the inner side in the longitudinal direction L, and so as to have the longitudinal direction length which is longer than the longitudinal direction length $D_6$ of the engagement portion 6.

When the compressed portion formation region 700 is disposed at such a position in this manner, especially in the portion Q on the inner side in the longitudinal direction L with respect to the engagement portion 6, not only the diaper for pets 1H can make it difficult for the portion which affects the adhesion to the engagement portion 6 to be bent, but also even if the portion Q on the inner side in the longitudinal direction L with respect to the engagement portion 6 is bent, the possibility of the bent portion being adhered to the engagement portion 6 can be more reliably decreased. That is, the diaper for pets 1H can make it difficult for the event as shown in FIG. 24(c) in the conventional absorbent article for animals to be caused more reliably.

Figure 20:
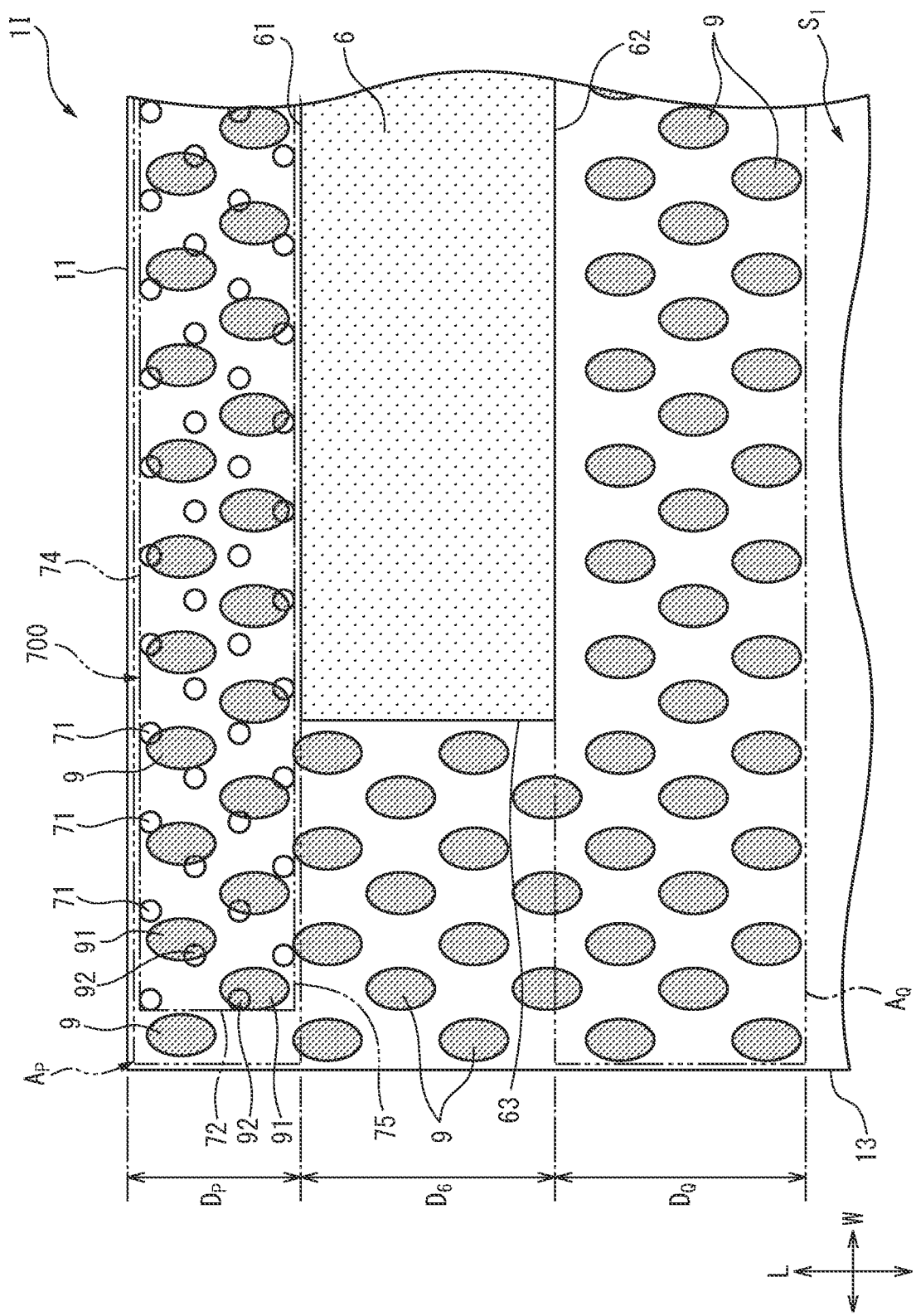
FIG. 20 is a principal portion enlarged plan view of the diaper for pets 1I according to one or more embodiments in an expanded state viewed from the first surface side in the thickness direction T.

FIG. 20 is a principal portion enlarged plan view of the diaper for pets 1I according to one or more embodiments in an expanded state viewed from the first surface side $D_1$ in the thickness direction T.

In the diaper for pets 1I according to one or more embodiments, as shown in FIG. 20, the surface on the second surface side $D_2$ of the back sheet 3 which is formed by a nonwoven fabric and forms the first surface $S_1$, and the surface on the first surface side $D_1$ of the back film 31 which is formed by a liquid impermeable member disposed on the second surface side $D_2$ of the back sheet 3 are joined by a plurality of joining portions 9, and further, the plurality of joining portions 9 include the non-overlapping portion 91 which does not overlap with the compressed portions 71 in a plan view, in the compressed portion formation region 700 disposed in the above described flap portion P.

Incidentally, in one or more embodiments, the plurality of joining portions 9 include, as shown in FIG. 20, the overlapping portion 92 which partially overlaps with the compressed portions 71 other than the above described non-overlapping portion 91.

In one or more embodiments, when the joining portions 9 which join a surface on a first surface side $D_1$ of the back film 31 and a surface on a second surface side $D_2$ of the back sheet 3 includes in the above described compressed portion formation region 700, a non-overlapping portion 91 which does not overlap with the compressed portions in a plan view, the non-overlapping portion 91 can make it difficult for the back sheet 3 to be lifted up between the adjacent compressed portions 71 in the compressed portion formation region 700, whereby even when the above described flap portion P is bent and the compressed portion formation region 700 comes close to the engagement portion 6, since it is difficult not only for the above described compressed portions 71 but also for the non-overlapping portion 91 to be in contact with the above described engagement portion 6, the possibility of the compressed portion formation region 700 being adhered to the engagement portion 6 can be more reliably decreased.

Incidentally, such effects can also be exhibited in the same manner even when the compressed portion formation region 700 is disposed in the portion Q on the inner side in the longitudinal direction L with respect to the engagement portion 6.

Incidentally, in one or more embodiments, the plurality of joining portions may include overlapping portions which partially overlap with the compressed portions as long as the plurality of joining portions include the above described non-overlapping portion, and further, all of the joining portions may include the non-overlapping portion or only a portion of the joining portions may include the non-overlapping portion.

Further, in one or more embodiments, each of the plurality of joining portions 9 has, as shown in FIG. 20, in a plan view, a substantially oval dot-like outer shape, and is disposed in a staggered form. When the plurality of joining portions 9 are disposed in such a staggered form, in the above described compressed portion formation region 700, the non-overlapping portion 91 which does not overlap with the compressed portions 71 can be disposed evenly overall, whereby the effect of the diaper for pets 1I according to one or more embodiments can be exhibited more advantageously.

In one or more embodiments, the outer shape and the disposing manner of each of the joining portions are not particularly limited. For example, in one or more embodiments, the joining portions, in a plan view, may be formed in an arbitrary outer shape such as a circular shape, a triangular shape; a rectangular shape such as a square, a diamond shape, etc.; a cross shape; one or a plurality of linear shapes (for example, continuous or non-continuous straight line, wavy line, zigzag line, etc.); one or a plurality of belt-like shapes; design drawings of various symbols, patterns, animals and plants, various characters, etc., and can be disposed in an arbitrary form such as grid, stripe, spiral, and random, etc.

Incidentally, in one or more embodiments, the number of the joining portions and the size of each of the joining portions, etc., are not particularly limited. In one or more embodiments, an arbitrary number and the size, etc., of each of the joining portions, in accordance with the desired joining strength, etc., may be adopted.

In one or more embodiments, the forming means of the above described joining portions, that is, the joining means to join at least the surface on the first surface side of the liquid impermeable member and the surface on the second surface side of the nonwoven fabric which forms the first surface is not particularly limited. In one or more embodiments, an arbitrary joining means known in the art (for example, a heat fusion means, a bonding means by using a hot melt adhesive agent, etc.) may be adopted.

Further, the absorbent article for animals according to one or more embodiments may include, at a different position from that of the above described compressed portion formation region which is disposed so as to overlap with the engagement portion peripheral region, a compressed portion formation region which is different from the above described compressed portion formation region.

Hereinbelow, such an absorbent article for animals which includes another compressed portion formation region is explained in detail while exemplifying other embodiments which are different from the above described embodiments. Incidentally, in one or more embodiments, the configurations other than those different from the above described embodiments are basically the same as those in the above described embodiments, and thus the explanations thereof will be omitted.

Figure 21:
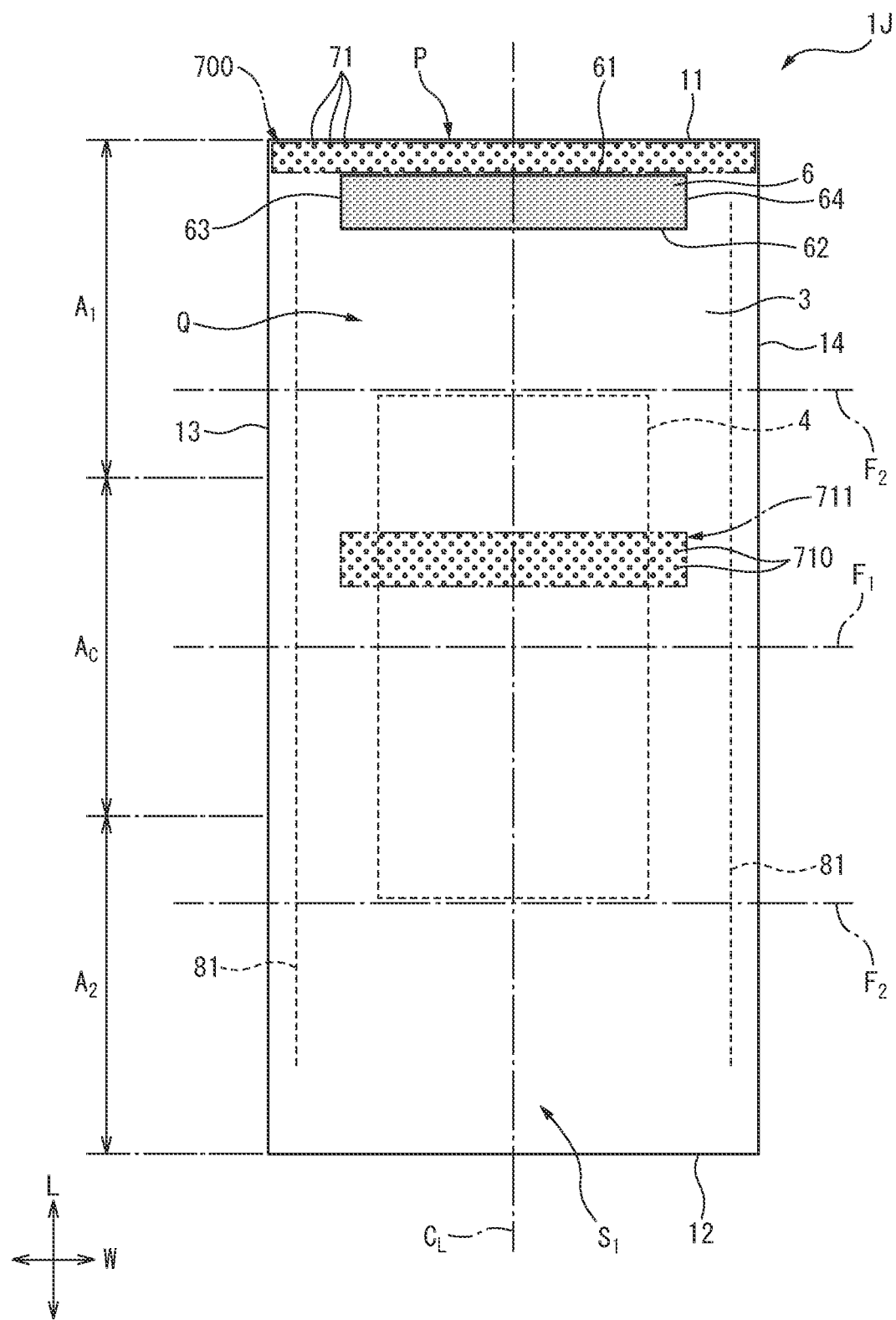
FIG. 21 is a plan view of the diaper for pets 1J according to one or more embodiments in an expanded state viewed from the first surface side in the thickness direction T.
Figure 22A:
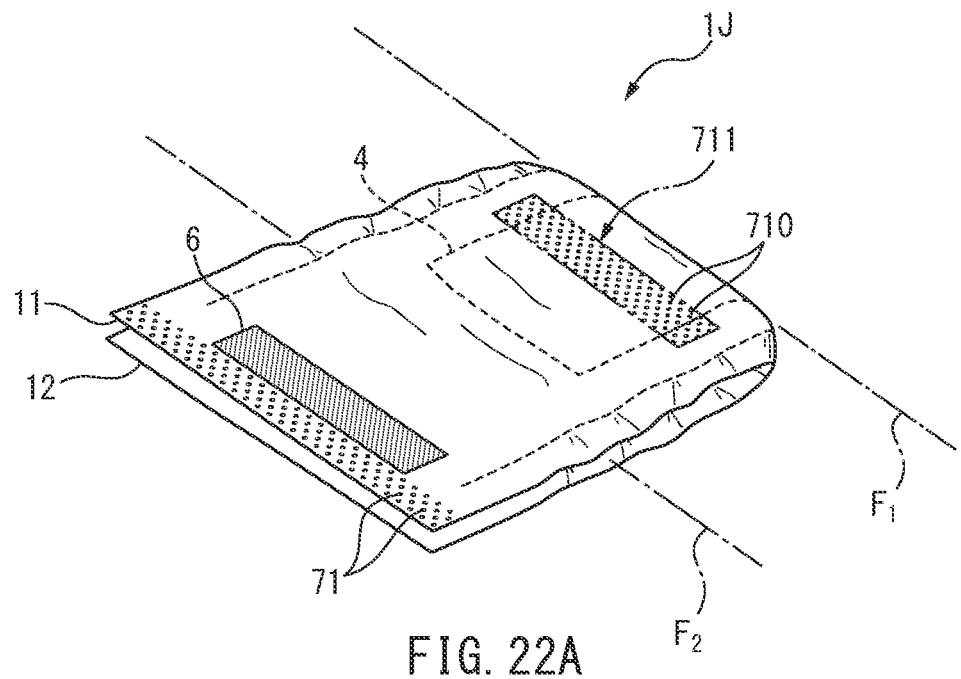
FIG. 22A is a perspective view which shows a state in which the diaper for pets 1J is folded at the first bending line $F_1$ so that the second surface $S_2$ is on the inner side according to one or more embodiments.
Figure 22B:
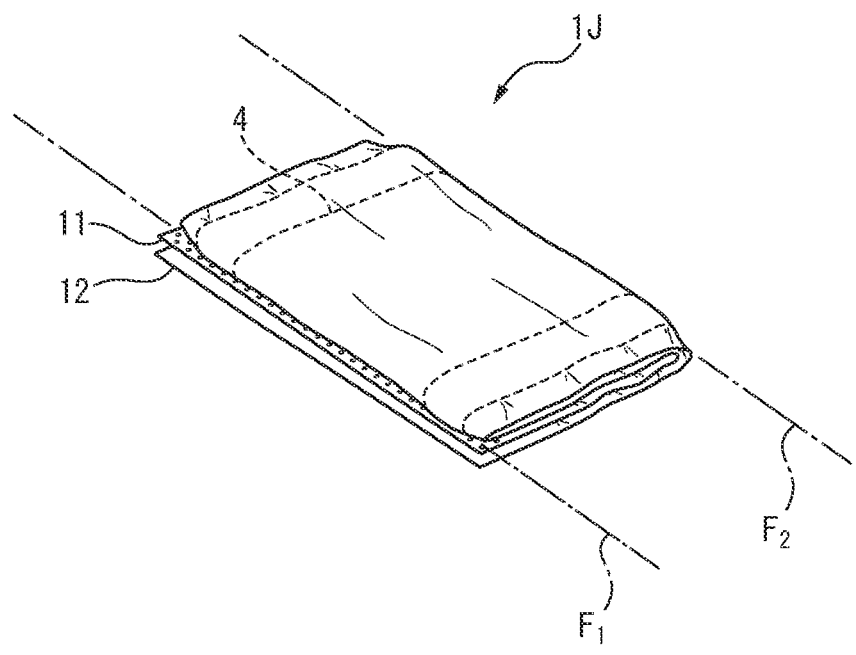
FIG. 22B is a perspective view which shows a state in which the diaper for pets 1J that has been folded at the first bending line $F_1$ is further folded at the second bending line $F_2$ so that the engagement portion 6 is to be located on the inner side according to one or more embodiments.
Figure 23:
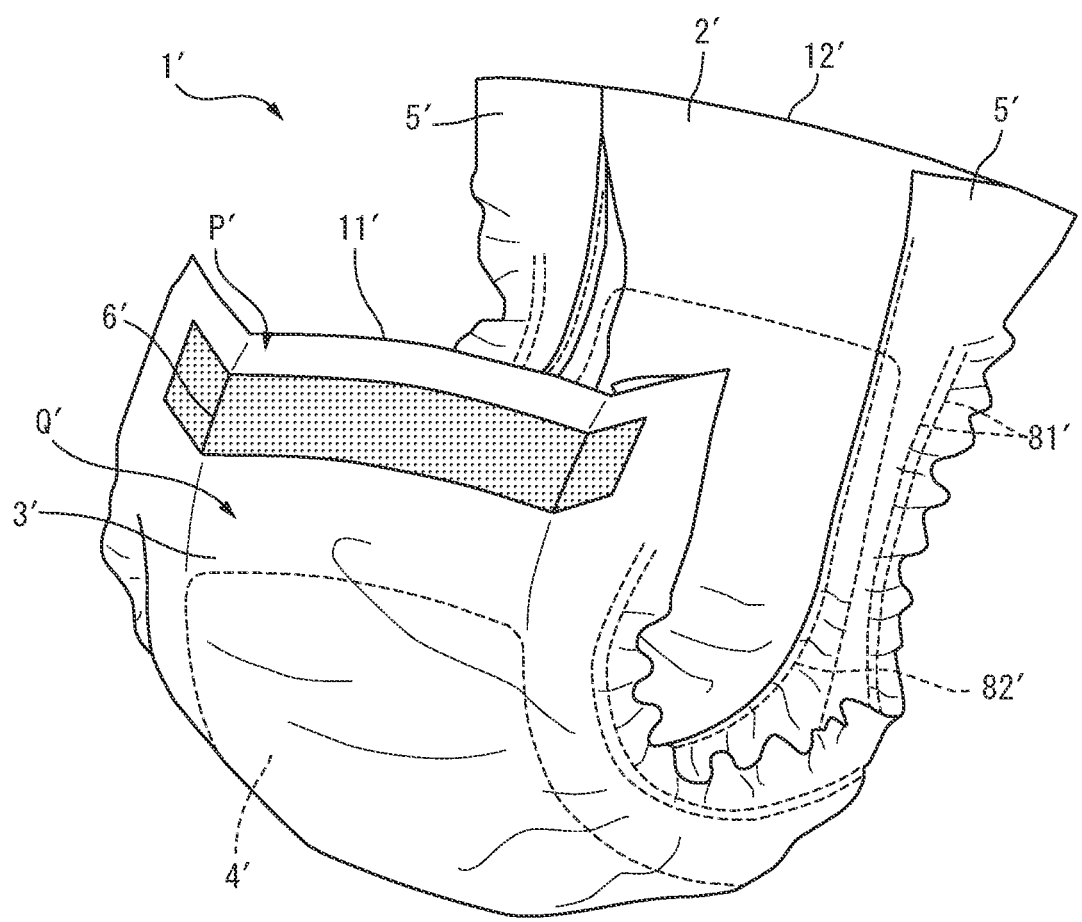
FIG. 23 is a perspective view of the conventional diaper for pets 1' according to one or more embodiments.

FIG. 21 is a plan view of the diaper for pets 1J according to one or more embodiments in an expanded state viewed from the first surface side $D_1$ in the thickness direction T. Further, FIG. 22(a) is a perspective view which shows a state in which the diaper for pets 1J is folded at the first bending line $F_1$ so that the second surface $S_2$ is on the inner side, and FIG. 22(b) is a perspective view which shows a state in which the diaper for pets 1J that has been folded at the first bending line $F_1$ is further folded at the second bending line $F_2$ so that the engagement portion 6 is to be located on the inner side.

The diaper for pets 1J according to one or more embodiments includes, as shown in FIG. 21 and FIG. 22, in a plan view, the first bending line $F_1$ which extends in the width direction W and overlaps with the longitudinal direction central axis line $C_W$ that extends in the width direction W, for folding the diaper for pets 1J so that the second surface $S_2$ is to be located on the inner side, and two second bending lines $F_2$ which extend in the width direction W and which are positioned, between the one side edge 11 in the longitudinal direction L of the diaper for pets 1J and the first bending line $F_1$, and between the other side edge 12 in the longitudinal direction L of the diaper for pets 1J and the first bending line $F_1$, for further folding the diaper for pets 1J which has been folded at the first bending line $F_1$ so that the engagement portion 6 is to be located on the inner side, and further, such a diaper for pets 1J further includes, the inner side compressed portion formation region 711 which includes the plurality of compressed portions 710 that are depressed from the first surface $S_1$ in the thickness direction T, in the first surface $S_1$ of the region that is in a symmetrical relationship with the engagement portion 6, with the second bending line $F_2$ that is positioned between the one side edge 11 in the longitudinal direction L of the diaper for pets 1J and the first bending line $F_1$ as a target axis.

The diaper for pets 1J according to one or more embodiments further includes, as shown in FIG. 21, separately from the compressed portion formation region 700 which is disposed so as to overlap with the above described engagement portion peripheral region $A_P$, the inner side compressed portion formation region 711 which includes the plurality of compressed portions 710 that are depressed from the first surface $S_1$ in the thickness direction T, in the first surface $S_1$ of a region that is in a symmetrical relationship with the engagement portion 6, with the above described second bending line $F_2$ as the target axis, whereby as shown in FIG. 22, even when a plurality of diapers for pets 1J are folded at the first bending line $F_1$ and the second bending lines $F_2$ so as to be packaged, it is difficult for the above described engagement portion 6 to be engaged with the inner side compressed portion formation region 711 in the folded diapers for pets 1J, and it is difficult for the engagement force of the engagement portion 6 to be decreased.

In one or more embodiments, the above described inner side compressed portion formation region can be formed in the same form as the compressed portion formation region which is disposed so as to overlap with the engagement portion peripheral region.

Incidentally, the method of manufacturing the absorbent article for animals by using the above described various configurational members is not particularly limited, and an arbitrary manufacturing method known in the art can be adopted. For example, the diaper for pets 1 according to one or more embodiments can be manufactured by overlapping various members which configure the diaper for pets 1, that is, by overlapping the pair of side sheets 5, 5 on which the pair of elastic members for three-dimensional gather formation 82, 82 are arranged at the end portions on the inner side in the width direction W, the top sheet 2, the absorbent body 4, the back film 31, the pair of elastic members for side portion gather formation 81, 81, the back sheet 3 and the engagement portion 6, in the disposing manner as shown in FIG. 15 to FIG. 16, and by joining the same by an arbitrary joining means (for example, a bonding method by using a hot melt adhesive agent, a heat sealing method, and an ultrasonic bonding method, etc.), by compressing the predetermined position on the surface of the first surface side $D_1$ of the back sheet 3 by using heated or unheated embossing means for compressed portion formation including a plurality of protruded portions either before, at the same time as, or after the joining, and by forming the above described plurality of compressed portions 71 (that is, the compressed portion formation region 700).

Embodiments of the present invention can be applied to various absorbent articles for animals for example, such as a (light) incontinence pad for pets, etc., other than the diaper for pets according to the above described embodiments. Further, the absorbent article for animals according to one or more embodiments of the present invention is not limited to the above described embodiments. In one or more embodiments, suitable combination, substitution, and modification, etc., are possible. Incidentally, in the present description, the ordinal numbers such as "the first", and "the second", etc., are for the purpose of distinguishing the matter to which such ordinal numbers are allotted, and they do not mean the order, the priority, the significance, etc., of each matter.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

1 diaper for pets (absorbent article for animals)
2 top sheet (nonwoven fabric which forms second surface)
3 back sheet (nonwoven fabric which forms first surface)
31 back film (liquid impermeable member)
4 absorbent body
5 side sheet
6 engagement portion
7 flap portion
70 surplus portion
71 compressed portion

What is claimed is:

1. An absorbent article for animals that includes a longitudinal direction, a width direction, and a thickness direction that are mutually orthogonal to each other, the absorbent article comprising:
   a first nonwoven fabric that forms a first surface in the thickness direction;
   a second nonwoven fabric that forms a second surface in the thickness direction that is on an opposite side of the first surface, and that is attached to an animal such that the longitudinal direction is disposed along a waist of the animal;
   in a plan view, between a first side edge and a second side edge of the absorbent article in the longitudinal direction, a first region, a center region, and a second region that divide the absorbent article into three equal portions in the longitudinal direction, wherein
      the first side edge of the absorbent article extends along the width direction in the first region, and
      the second side edge of the absorbent article extends along the width direction in the second region;
   an engagement portion that extends along the width direction in the first surface of the first region and that engages in a detachable manner with the second surface of the second region, wherein
      the engagement portion has a first side edge and a second side edge that extend along the width direction, and
      the first side edge of the engagement portion is closer to the first side edge of the absorbent article than is the second side edge of the engagement portion; and
   a flap portion that extends along the width direction in the first region, wherein the flap portion is between the first side edge of the engagement portion and the first side edge of the absorbent article, wherein
      a longitudinal direction length of the flap portion is longer than a longitudinal direction length of the engagement portion.

2. The absorbent article according to claim 1, wherein the engagement portion includes, in the width direction, an engagement element non-disposed portion in which an engagement element is not disposed.

3. The absorbent article according to claim 2, wherein the engagement portion includes, in the width direction, an engagement element crushed portion.

4. The absorbent article according to claim 2, further comprising:
   in a plan view, two bending lines that extend in the longitudinal direction at positions that pass the first side edge and the second side edge of the engagement portion in the width direction, or at positions on an outer side in the width direction with respect to the first side edge and the second side edge of the engagement portion, wherein
      each of a first side end portion and a second side end portion of the absorbent article in the width direction is folded toward a second surface side at each of the bending lines.

5. The absorbent article according to claim 2, further comprising:
   in a plan view, an elastic member that extends in the longitudinal direction at each of a first side end portion and a second side end portion of the absorbent article in the width direction, wherein
   each of the elastic members overlaps with the flap portion in a plan view.

6. The absorbent article according to claim 1, wherein the engagement portion includes, in the width direction, an engagement element crushed portion.

7. The absorbent article according to claim 3, wherein the engagement element crushed portion is disposed at a position that includes at least one of the first side edge and the second side edge of the engagement portion in the width direction.

8. The absorbent article according to claim 1, further comprising:
   in a plan view, two bending lines that extend in the longitudinal direction at positions that pass the first side edge and the second side edge of the engagement portion in the width direction, or at positions on an outer side in the width direction with respect to the first side edge and the second side edge of the engagement portion, wherein
      each of a first side end portion and a second side end portion of the absorbent article in the width direction is folded toward a second surface side at each of the bending lines.

9. The absorbent article according to claim 1, further comprising:
   in a plan view, an elastic member that extends in the longitudinal direction at each of a first side end portion and a second side end portion of the absorbent article in the width direction, wherein
   each of the elastic members overlaps with the flap portion in a plan view.

10. The absorbent article according to claim 1, further comprising:
   an absorbent body that is disposed between the first nonwoven fabric and the second nonwoven fabric and that extends across from the first region to the second region in a plan view, wherein
   a first side edge of the absorbent body that extends along the longitudinal direction overlaps with the engagement portion in the thickness direction.

* * * * *